US009096879B2

(12) United States Patent
Khetan et al.

(10) Patent No.: US 9,096,879 B2
(45) Date of Patent: Aug. 4, 2015

(54) METHOD OF SUPPLEMENTING CULTURE MEDIA TO PREVENT UNDESIRABLE AMINO ACID SUBSTITUTIONS

(75) Inventors: Anurag Khetan, Lexington, MA (US);
Yao-ming Huang, San Diego, CA (US);
Jana Dolnikova, Waltham, MA (US);
Nels Pederson, Mansfield, MA (US);
Helena Yusuf-Makagiansar, San Diego, CA (US); Paul Chen, Belmont, MA (US); Thomas Ryll, Lexington, MA (US)

(73) Assignee: BIOGEN MA INC., Cambridge, MA (US)

( * ) Notice: Subject to any disclaimer, the term of this patent is extended or adjusted under 35 U.S.C. 154(b) by 409 days.

(21) Appl. No.: 13/511,203

(22) PCT Filed: Nov. 24, 2009

(86) PCT No.: PCT/US2009/065803
§ 371 (c)(1),
(2), (4) Date: Sep. 6, 2012

(87) PCT Pub. No.: WO2011/065940
PCT Pub. Date: Jun. 3, 2011

(65) Prior Publication Data
US 2013/0096283 A1    Apr. 18, 2013

(51) Int. Cl.
C07K 14/435 (2006.01)
C12N 5/00 (2006.01)
C12N 5/02 (2006.01)
C12N 5/071 (2010.01)
C12N 15/00 (2006.01)
C12N 15/06 (2006.01)
C12N 15/09 (2006.01)
C12P 21/02 (2006.01)
C07K 16/24 (2006.01)

(52) U.S. Cl.
CPC .............. C12P 21/02 (2013.01); C07K 16/241 (2013.01); C07K 16/24 (2013.01); C07K 2317/41 (2013.01); C07K 2317/515 (2013.01); C12N 2500/32 (2013.01); C12N 2510/02 (2013.01)

(58) Field of Classification Search
USPC .............................. 435/325, 252.3, 69.3, 69.4
See application file for complete search history.

(56) References Cited

U.S. PATENT DOCUMENTS

| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,821,089 A | 10/1998 | Gruskin et al. |
| 6,492,508 B1 | 12/2002 | Gruskin et al. |
| 6,936,441 B2 | 8/2005 | Reiter et al. |
| 2006/0240004 A1* | 10/2006 | Burkly et al. ............... 424/143.1 |
| 2008/0108106 A1* | 5/2008 | Wang et al. .................... 435/69.1 |
| 2008/0241163 A1 | 10/2008 | Burkly et al. |
| 2011/0091936 A1* | 4/2011 | Gawlitzek et al. ........... 435/69.3 |

FOREIGN PATENT DOCUMENTS

| WO | WO 87/00195 A1 | 1/1987 |
| WO | WO 90/03430 A1 | 4/1990 |
| WO | WO 2006/130374 A2 | 12/2006 |
| WO | WO 2009-047007 A1 * | 6/2009 |

OTHER PUBLICATIONS

Gong et al. Regulation of asparagine synthetase gene expression by amino acid starvation. Molecular and Cellular Biology vol. 11/12:6059-6066 (Dec. 1991).*
An, S., and Musier-Forsyth, K., "Cys-tRNA$^{Pro}$ Editing *Haemophilus influenzae* YbaK via a Novel Synthetase•YbaK•tRNA Ternary Complex," *J. Biol. Chem.* 280(41):34465-34472, The American Society for Biochemistry and Molecular Biology, Inc., United States (2005).
Andrulis, I.L., et al., "Asparaginyl-tRNA Aminoacylation Levels and Asparagine Synthetase Expression in Cultured Chinese Hamster Ovary Cells," *J. Biol. Chem.* 254(21):10629-10633, American Society for Biochemistry Inc., United States (1979).
Apostol, I., et al., "Incorporation of Norvaline at Leucine Positions in Recombinant Human Hemoglobin Expressed in *Escherichia coli*," *J. Biol. Chem.* 272(46):28980-28988, American Society for Biochemistry and Molecular Biology, Inc., United States (1997).
Arfin, S.M., et al., "A role for asparaginyl-tRNA in the regulation of asparagine synthetase in a mammalian cell line," *Proc. Natl. Acad. Sci. U.S.A.* 74(6):2367-2369, National Academy of Science, United States (1977).
Barker, D.G., and Bruton, C.J., "The Fate of Norleucine as a Replacement for Methionine in Protein Synthesis," *J. Mol. Biol.* 133:217-231, Academic Press Inc., United States (1979).
Barnes, D. and Sato, G., "Methods for Growth of Cultured Cells in Serum-Free Medium," *Analytical Biochemistry* 102:255-270, Academic Press, Inc., United States (1980).
Berthet-Colominas, C., et al., "The crystal structure of asparaginyl-tRNA synthetase from *Thermus thermophilus* and its complexes with ATP and asparaginyl-adenylate: the mechanism of discrimination between asparagine and aspartic acid," *EMBO J* 17(10):2947-2960, Oxford University Press, England (1998).

(Continued)

*Primary Examiner* — Elizabeth C Kemmerer
*Assistant Examiner* — Regina M Deberry
(74) *Attorney, Agent, or Firm* — Sterne, Kessler, Goldstein and Fox PLLC

(57) ABSTRACT

The present invention relates to methods of reducing substitution of amino acids during the production of polypeptides of interest in mammalian cells. By varying the concentration of amino acids in the culture medium, heterogeneity of the polypeptide's amino acid sequence is decreased, leading to higher yields of functional protein.

17 Claims, 13 Drawing Sheets

(56) References Cited

OTHER PUBLICATIONS

Birch, J.R., and Racher, A.J., "Antibody production," *Adv. Drug Delic. Rev.* 58:671-685, Elsevier B.V., Netherlands (2006).

Bogosian, G., et al., "Biosynthesis and Incorporation into Protein of Norleucine by *Escherichia coli*," *J. Biol. Chem.* 264(1):531-539, American Society for Biochemistry and Moleculare Biology, Inc., United States (1989).

Brinkmann, U., et al., "High-level expression of recombinant genes in *Escherichia coli* is dependent on the availability of the *dnaY* gene product," *Gene* 85:109-114, Eslevier Science Publishers B.V., Netherlands (1989).

Calderone, T.L., et al., "High-Level Misincorporation of Lysine for Arginine at AGA Codons in a Fusion Protein Expressed in *Escherichia coli*," *J. Mol. Biol.* 262:407-412, Academic Press Ltd., England (1996).

Cusack, S., "Eleven down and and nine to go," *Nat. Struct. Biol.* 2(10):824-831, Nature Publishing Group, England (1995).

Dorai, H., et al., "Investigation of Product Microheterogeneity," *Bioprocess International* 5:66-72, Informa Healthcare, England (2007).

George, E., et al., "First observation of haemoglobin Malay $\alpha_2 B_2$ 26 (B1) Asn → Ser-A case report," *Med. J. Malaysia* 44:259-262, Malaysian Medical Association, Malaysia (1989).

Graham, F.L., et al., "Characteristics of a Human Cell Line Transformed by DNA from Human Adenovirus Type 5," *J. Gen. Virol.* 36:59-72, Cambridge University Press, England (1977).

Gruic-Sovulj, I., et al., "Hydrolysis of non-cognate aminoacyl-adenylates by a class II aminoacyl-tRNA synthetase lacking an editing domain," *FEBS Lett.* 581-5110-5114, Elsevier B.V., Netherlands (2007).

Gruic-Sovulj, I., et al., "tRNA-dependent Aminoacyl-adenylate Hydrolysis by a Nonediting Class I Aminoacyl-tRNA Synthetase," *J. Biol. Chem.* 280(25):23978-23986, The American Society for Biochemistry and Molecular Biology, Inc., United states (2005).

Ham, R.G., and Wallace, W.L., "Media and Growth Requirements," in *Methods in Enzymology*, vol. 58, Jakoby, W.B., and Pastan, I.H., eds., pp. 44-93, Academic Press, Inc., San Diego, United States (1979).

Harris, R.J., et al., "Assessing Genetic Heterogeneity in Production Cell Lines: Detection by Peptide Mapping of a Low Level Tyr to Gln Sequence Variant in a Recombinant Antibody," *Bio/Technology* 11:1293-1297, Nature Publishing Group, England (1993).

Hati, S., et al., "Pre-transfer Editing by Class II Prolyl-tRNA Synthetase: Role of aminoacylation active site in 'selective release' of noncognate amino acids," *J. Biol. Chem.* 281(38):27862-27872, The American Society for Biochemistry and Molecular Biology, Inc., United States (2006).

Ibba, M., and Söll, D., "Quality Control Mechanisms During Translation," *Science* 286:1893-1897, American Association for the Advancement of Science, United States (1999).

Ishitobi, M., et al., "Mutational analysis of *BARD1* in familial breast cancer patients in Japan," *Cancer Lett.* 200:1-7, Elsevier Ireland Ltd., Ireland (2003).

Jnaoui, K., et al., "Mutations That Affect the Tropism of DA and GDVII Strains of Theiler's Virus In Vitro Influence Sialic Acid Binding and Pathogenicity," *Journal of Virology* 76(16):8138-8147, American Society for Microbiology, United States (2002).

Johnston, T.C., et al., "Codon specificity of starvation induced misreading," *Mol. Gen. Genet.* 195:459-465, Springer-Verlag, Germany (1984).

Kane, J.F., "Effects of rare codon clusters on high-level expression of heterologous proteins in *Escherichia coli*," *Current Opinion of Biotechnology* 6:494-500, Current Biology Ltd, England (1995).

Kaye, E.M., et al., "β-Galactosidase Gene Mutations in Patients with Slowly Progressive $G_{M1}$ Gangliosidosis," *J. Child Neurol.* 12:242-247, PSG Pub. Co., United States (1997).

Klannemark, M., et al., "Interaction between the Asn291Ser variant of the *LPL* gene and insulin resistance on dyslipidaemia in high risk individuals for Type 2 diabetes mellitus," *Diabetic Medicine* 17:599-605, Diabetes UK, England (2000).

Lagerkvist, U., "'Two out of three': An alternative method for codon reading," *Proc. Natl. Acad. Sci. U.S.A.* 75(4):1759-1762, National Academy of Science, United States (1978).

Laughrea, M., et al., "Mistranslation in twelve *Escherichia coli* ribosomal proteins: Cysteine misincorporation at neutral amino acid residues other than tryptophan," *Eur. J. Biochem.* 169:59-64, FEBS, Netherlands (1987).

Lee, J.W., et al. "Editing-defective tRNA synthetase causes protein misfolding and neurodegeneration," *Nature* 443:50-55, Nature Publishing Group, England (2006).

Lincecum, T.L., Jr., et al., "Structural and Mechanistic Basis of Pre- and Posttransfer Editing by Leucyl-tRNA Synthetase," *Molecular Cell* 11:951-963, Cell Press, United States (2003).

Low, D., et al., "Future of antibody purification," *Journal of Chromatography B* 848:48-63, Elsevier B.V., Netherlands (2007).

Lu, H.S., et al., "Identification of unusual replacement of methionine by norleucine in recombinant interleukin-2 produced by *E. coli*," *Biochemical and Biophysical Research Communications* 156:(2):807-813, Academic Press, Inc., United States (1988).

Lu, H.S., et al., "Isolation and Characterization of Three Recombinant Human Granulocyte Colony Stimulating Factor His → Gln Isoforms Produced in *Escherichia coli*," *Protein Expression and Purification* 4:465-472, Academic Press, United states (1993).

Lustig, F., et al., "Codon Reading and Translational Error: Reading of the Glutamine and Lysine Codons During Protein Synthesis in Vitro," *J. Biol. Chem.* 256(6):2635-2643, American Society of Biological Chemists, United States (1981).

Mascarenhas, A.P., et al., "Fidelity Mechanisms of the Aminoacyl-tRNA Synthetases," in *Protein Engineering*, Edition 1, Köhrer, C., and RajBhandary, U.L., eds., pp. 155-203, Springer-Verlag, berlin, Germany (2009).

Mather, J.P., "Establishment and Characterization of Two Distinct Mouse Testicular Epithelial Cell Lines," *Biology of Reproduction* 23:243-252, Society for the Study of Reproduction, United States (1980).

Mather, J.P., et al., "Culture of Testicular Cells in Hormone-Supplemented Serum-Free Medium," *Annals N.Y. Acad Sci.* 383:44-68, New York Academy of Sciences, United States (1982).

McClendon, C.L., et al., "Fidelity of seryl-tRNA synthetase to binding of natural amino acids from HierDock first principles computations," *Protein Eng. Des. Sel.* 19(5):195-203, Oxford University Press, England (2006).

McNulty, D.E., et al., "Mistranslational errors associated with the rare arginine codon CGG in *Escherichia coli*," *Protein Expression and Purification* 27:365-374, Elsevier Science, United States (2002).

Newberry, K.J., et al., "Structural origins of amino acid selection without editing by cysteinyl-tRNA synthetase," *EMBO Journal* 21:2778-2787, European Molecular Biology Organization, England (2002).

Nomanbhoy, T.K., et al., "Transfer RNA-Dependent Translocation of Misactivated Amico Acids to Prevent Errors in Protein Synthesis," *Mol. Cell* 4:519-528, Cell Press, United States (1999).

Park, S.G., et al., "Aminoacyl tRNA synthetases and their connections to disease," *Proc. Natl. Acad. Sci.* 105(32):11043-11049, The National Academy of Sciences of the USA, United States (2008).

Parker, J., "Errors and Alternatives in Reading the Universal Genetic Code," *Microbiol. Rev.* 53(3):273-298, American Society for Microbiology, United States (1989).

Parker, J., and Friesen, J.D., "'Two out of Three' Codon Reading Leading to Mistranslation in vivo," *Molec. Gen. Genet.* 177:439-445, Springer-Verlag, Germany (1980).

Parker, J., et al., "Codon Usage and Mistranslation: In Vivo Basal Level Misreading of the MS2 Coat Protein Message," *J. Biol. Chem.* 258(16):10007-10012, American Society of Biological Chemists, United States (1983).

Parker, J., et al., "Stuttering: High-level mistranslation in animal and bacterial cells," *Proc. Natl. Acad. Sci. U.S.A.* 75(3):1091-1095, National Academy of Science, United States (1978).

Petersen, L.A., et al., "Effects of amino acid and trace element supplementation on pneumocandin production by *Glarea lozoyensis*: impact on titer, analogue levels, and the identification of new ana-

(56) References Cited

OTHER PUBLICATIONS logues of pneumocandin $B_0$," *Journal of Industrial Microbiology & Biotechnology* 26:216-221, Nature Publishing Group, England (2001).

Pöschl, E., et al., "Two non-contiguous regions contribute to nidogen binding to a single EGF-like motif of the laminin γ1 chain," *EMBO Journal* 13(16):3741-3747, Oxford University Press, England (1994).

Precup, J., and Parker, J., "Missense Misreading of Asparagine Codons as a Function of Codon Identity and Context," *J. Biol. Chem.* 262(23):11351-11355, The American Society for Biochemistry and Molecular Biology, Inc., United States (1987).

Reichert, J. M., et al., "Monoclonal antibody successes in the clinic," *Nat. Biotechnol.* 23(9):1073-1078, Nature Publishing Company, United States (2005).

Rosenberger, R.F., "Senescence and the accumulation of abnormal proteins," *Mutat. Res.* 256:255-262, Elsevier Science Publishers B.V., Netherlands (1991).

Rosenberger, R.F., "Translational Errors during Recombinant Protein Synthesis," *Dev. Biol. Stand.* 83:21-26, International Association of Biological Standardization, Switzerland (1994).

Rosenberg, R.F., and Holliday, R., "Recombinant therapeutic proteins and translational errors," *Trends Biotechnol.* 11:498-499, Elsevier Science Publishers, England (1993).

Ruan, B., and Söll, D., "The Bacterial YbaK Protein is a Cys-tRNA$^{Pro}$ and Cys-tRNA$^{Cys}$ Deacylase," *J. Biol. Chem.* 280(27):25887-25891, The American Society for Biochemistry and Molecular Biology, Inc., United States (2005).

Sankaranarayanan, R., and Moras, D., "The fidelity of the translation of the genetic code," *Acta Biochimica Polonica* 48(2);323-335, Polska Akademia Nauk. Komitet Biochemiczny, Poland (2001).

Santos, M.A.S., and Tuite, M.F., "New insights into mRNA decoding—implications for heterologous protein synthesis," *Trends Biotechnol.* 11:500-505, Elsevier Science Publishers Ltd, England (1993).

Schimmel, P., "Development of tRNA synthetases and connection to genetic code and disease," *Protein Science* 17:1643-1652, Cold Spring Harbor Laboratory Press, United States (2008).

Schneider, E.L., et al., "Amino Acid Substitution and Modification Resulting for *Escherichia coli* Expression of Recombinant *Plasmodium falciparum* Histidine-Rich Protein II," *Biochemistry* 44:987-995, American Chemical Society, United States (2005).

Scorer, C.A., et al., "Amino acid misincorporation during high-level expression of mouse epidermal growth factor in *Escherichia coli*," *Nucleic Acids Research* 19(13):3511-3516, Oxford University Press, England (1991).

Seetharam, R., et al., "Mistranslation in IGF-1 During Over-Expression of the Protein in *Escherichia coli* using a Synthetic Gene Containing Low Frequency Codons," *Biochemical and Biophysical Research Communications* 155(1):518-523, Academic Press, Inc., United States (1988).

Seewöster, T., and Lehmann, J., "Influence of targeted asparagine starvation on extra- and intracellular amino acid pools of cultivated Chinese hamster ovary cells," *Appl. Microbiol. Biotechnol.* 44:344-350, Springer-Verlag, Germany (1995).

Silvain, L.F., et al., "Insights into Editing from an Ile-tRNA Synthetase Structure with tRNA $^{Ile}$ and Mupirocin," *Science* 285:1074-1077, American Association for the Advancement of Science, United States (1999).

Spanjaard, R. A., et al., "Frameshift suppresion at tandem AGA and AGG codons by cloned tRNA genes: assigning a codon to *argU* tRNA and T4 tRNA$^{Arg}$," *Nucleic Acids Research* 18(17):5031-5036, Oxford University Press, England (1990).

Splan, K.E., et al., "In vitro assays for the determination of aminoacyl-tRNA synthetase editing activity," *Methods* 44(2):119-128, Academic Press, United States (2008).

Splan, K.E., et al., "Transfer RNA Modulates the Editing Mechanism Used by Class II Prolyl-tRNA Synthetase," *J. Biol. Chem.* 283(11):7128-7134, The American Society for Biochemistry and Molecular Biology, Inc., United States (2008).

Stanners, C.P., et al., "Effect of Extreme Amino Acid Starvation on the Protein Synthetic Machinery of CHO Cells," *J. Cell. Physiol.* 95:125-138, Wistar Institute of Anatomy and Biology, United States (1978).

Stevens, C., et al., "A Germ Line Mutation in the Death Domain of DAPK-1 Inactivates ERK-induced Apoptosis," *J. Biol. Chem.* 282(18):13791-13803, The American Society for Biochemistry and Molecular Biology, Inc., United States (2007).

Tsai, L.B., et al., "Control of Misincorporation of *de* Novo Synthesized Norleucine into Recombinant Interleukin-2 in *E. coli*," *Biochemical and Biophysical Research Communications* 156:733-739, Academic Press, Inc., United States (1988).

Tukalo, M., et al., "The crystal structure of leucyl-tRNA synthetase complexed with tRNA$^{Leu}$ in the post-transfer-editing conformation," *Nat. Struct. Mol. Biol.* 12(10):923-930, Nature Publishing Group, England (2005).

Urlaub, G., and Chasin, L.A., "Isolation of Chinese hamster cell mutants deficient in dihydrofolate reductase activity," *Proc. Natl. Acad. Sci. USA* 77(7):4216-4220, National Academy of Science, United States (1980).

Walz, R., et al., "Cortical malformations are associated with a rare polymorphism of cellular prion protein," *Neurology* 63:557-560, AAN Enterprises, Inc., United States (2004).

Wen, D., et al., "Discovery and Investigation of Misincorporation of Serine at Asparagine Positions in Recombinant Proteins Expressed in Chinese Hamster Ovary Cells," *J. Biol. Chem.* 284(47):32686-32694, The American Society for Biochemistry and Molecular Biology, Inc., Unites States (2009).

Wen, D., et al., "Disulfide Structure of the Leucine-rich Repeat C-Terminal Cap and C-Terminal Stalk Region of Nogo-66 Receptor," *Biochemistry* 44:16491-16501, American Chemical Society, United States (2005).

Wurm, F.M., "Production of recombinant protein therapeutics in cultivated mammalian cells," *Nat. Biotechnol.* 22(11):1393-1398, Nature Publishing Group, England (2004).

International Search Report and Written Opinion for International Application No. PCT/US2009/065803, United States Patent and Trademark Office, Alexandria, United States, mailed on May 26, 2010.

Altamirano, C., et al., "Strategies for fed-batch cultivation of t-PA producing CHO cells: substitution of glucose and glutamine and rational design of culture medium," *J. Biotechnol.* 110:171-179, Elsevier B.V., Netherlands (2004).

Harley, C.B., et al., "Model for Messenger RNA Translation during Amino Acid Starvation Applied to the Calculation of Protein Synthetic Error Rates," *J. Biol. Chem.* 256(21):10786-10794, The American Society for Biochemistry and Molecular Biology, Inc., United States (1981).

Jakubowski, H., and Goldman, E., "Editing of Errors in Selection of Amino Acids for Protein Synthesis," *Microbiological Reviews* 56(3):412-429, American Society for Microbiology, United States (1992).

Jonsson, M., et al., "Trunctuated Semenogelin I Binds Zinc and is Cleaved by Prostate-Specific Antigen," *Journal of Andrology* 27(4):542-547, American Society of Andrology, United States (Jul. 2006).

\* cited by examiner

METHOD OF SUPPLEMENTING CULTURE MEDIA TO PREVENT UNDESIRABLE AMINO ACID SUBSTITUTIONS

BACKGROUND OF THE INVENTION

1. Field of the Invention

The present invention relates to methods of reducing substitution of amino acids during the production of polypeptides of interest in mammalian cells. By varying the concentration of amino acids in the culture medium, heterogeneity of the polypeptide's amino acid sequence is decreased, leading to higher yields of protein of desired sequence.

2. Background

Substitutions of amino acids in the primary sequence of a protein are known to occur in nature. Typically, mutation occurs at the DNA level and then gets translated to the protein. During recombinant protein production, variant sequences including point mutations have been known to be introduced into production cell lines. For example, a variant form of an antibody gene sequence was found to be developed during the transfection of antibody light and heavy chain genes into chinese hamster ovary (CHO) cells (Harris, R. J. et al. *Bio-Technology* 11:1293-1297 (1993)).

Substitution can also occur during protein synthesis. Substitution during protein synthesis has been shown in ribosomal and non-ribosomal synthesis of peptides and proteins in prokaryotic systems. Mistranslations can be result of aberrant initiation, a frame shift, a missense error, tRNA hopping, or a termination bypass (Santos and Tuite, *Trends Biotech.* 11:500-505 (1993)). Imbalances in translation machinery typically impact the expression levels at which the protein of interest is expressed. In extreme cases of imbalance, increased protein heterogeneity due to misincorporation of amino acids has been observed.

The present invention reports on recombinant expression of polypeptides of interest in mammalian cells wherein a depletion of particular amino acids during synthesis triggers misincorporation.

BRIEF SUMMARY OF THE INVENTION

The present invention provides a method for reducing substitution of a first amino acid by a second amino acid during translation of a polypeptide of interest in an eukaryotic cell, comprising culturing the cell in growth media that is supplemented with the first amino acid, or a metabolic precursor thereof, in an amount sufficient to reduce amino acid substitution. In some embodiments, the first amino acid is an essential amino acid arginine, histidine, isoleucine, leucine, lysine, methionine, phenylalanine, threonine, tryptophan or valine. In another embodiment, the first amino acid is a non-essential amino acid present in limiting concentrations. In another embodiment, the first amino acid is derived from another amino acid. In one embodiment, the first amino acid is glutamine or asparagine. In another embodiment, the second amino acid is serine. In yet another embodiment, the first amino acid is asparagine, and the second amino acid is serine.

In one embodiment, the first amino acid is provided in the basal media during the growth or production phase. In one embodiment, the first amino acid is provided during the production phase. In another embodiment, the cell is maintained as a batch culture, fed-batch culture, or a perfusion culture. In a further embodiment, the first amino acid is provided in the feed media of a fed-batch culture. In yet another embodiment, the first amino acid is added prior to depletion.

In one embodiment, the first amino acid is added at a concentration greater than 0.1 mM. In another embodiment, the first amino acid is added at a concentration from about 1 mM to about 10 mM. In another embodiment, the first amino acid is added at a concentration from about 1 mM to about 6 mM. In another embodiment, the first amino acid is added at a concentration of about 3 mM. In yet another embodiment, the first amino acid is added at a concentration of about 6 mM.

In one embodiment, the eukaryotic cell producing the polypeptide of interest is a mammalian cell. In one embodiment, the mammalian cell is a chinese hamster ovary (CHO), monkey kidney CV1, monkey kidney COS, human lens epithelium, human embryonic kidney, baby hamster kidney, african green monkey kidney, human cervical carcinoma, canine kidney, buffalo rat liver, human lung, human liver, mouse mammary tumor, hybridoma or myeloma cell lines. In one embodiment, the myeloma cell line is selected from the group consisting of NS0, Sp2/0, and Ag8653.

In one embodiment, the first amino acid is provided at multiple intervals.

In one embodiment, the cell producing the polypeptide of interest is grown on a large scale. In one embodiment, the cell is grown in a bioreactor. In one embodiment, the cell is grown in shaker flasks.

In one embodiment, the polypeptide of interest is an antibody, antibody fragment, enzyme, receptor, hormone, regulatory factor, growth factor, antigen, or binding agent. In one embodiment, the polypeptide of interest comprises a high frequency of said first amino acid relative to the frequency of the other amino acids.

In one embodiment, the antibody or fragment thereof is selected from the group consisting of: monoclonal, bispecific, chimeric, primatized, humanized, human, Fc, Fab fragment, Fab' fragment, $F(ab)_2$ fragment, Fv fragment, single chain antibody. In one embodiment, the antibody specifically binds TWEAK. In one embodiment, the antibody comprises: (a) a heavy chain variable region having at least 90% sequence identity to SEQ ID NO:1; and/or (b) a light chain variable region having at least 90% sequence identity to SEQ ID NO:3. In one embodiment, the antibody comprises: (a) a heavy chain variable region comprising SEQ ID NO:1; and (b) a light chain variable region comprising SEQ ID NO:3.

In one embodiment, less than about 3% of the first amino acid residues are substituted by the second amino acid. In one embodiment, less than about 1% of the first amino acid residues are substituted by the second amino acid. In one embodiment, less than about 0.1% of the first amino acid residues are substituted by the second amino acid.

In one embodiment, the method further comprises isolating the polypeptide of interest.

The invention also provides for a method for reducing substitution of a first amino acid by a second amino acid during translation of a polypeptide of interest in an eukaryotic cell, comprising culturing the cell in growth media in which the amount of the second amino acid is reduced. In one embodiment, the first amino acid is asparagine, and the second amino acid is serine.

The invention also provides a method for reducing substitution of asparagine by serine during translation of a polypeptide of interest in an eukaryotic cell, comprising culturing the cell in growth media in which the amount of asparagine, or a metabolic precursor thereof, is increased and the amount of serine is decreased as compared to the basal media formulation.

The invention also provides an antibody having less than about 3% substitutions of a first amino acid by a second amino acid produced by a process comprising the steps of: (a) growing a mammalian cell expressing the antibody in a culture medium, (b) monitoring at least one characteristic of said medium, and (c) supplementing the culture medium with the first amino acid in an amount sufficient to reduce substitution by the second amino acid.

The invention also provides an antibody or fragment thereof that binds to a TWEAK molecule, comprising at least 1, 2, 3, 4, 5 or 6 CDR of SEQ ID NOs 1 and 3, wherein at least one CDR comprises a serine substitution of an asparagine. In one embodiment, the antibody or fragment thereof comprises a heavy chain variable region having at least 90% sequence identity to SEQ ID NO: 1 and/or a light chain variable region having at least 90% sequence identity to SEQ ID NO: 3. In another embodiment, the antibody or fragment thereof comprises SEQ ID NO: 1 and 3, and comprising at least 1, 2, 3, 4, 5, 6, 7, 8, 9, 10, 11, 12, 13, 14, 15, 16, 17, 18, 19, or 20 substituted asparagines. In a further embodiment, the asparagines are substituted by serine. In yet another embodiment, each asparagine is replaced by a serine. In one embodiment, the antibody or fragment binds to the same epitope as, or competes with the binding to Tweak of, or crossblocks the binding of, an antibody comprising SEQ ID NO: 1 and 3. In a further embodiment, the antibody is a scFv.

The invention also provides a composition comprising an antibody or fragment thereof binding to a Tweak molecule, wherein less than about 10%, 5%, 3%, 1%, 0.5%, 0.3%, 0.1% of the antibodies or fragments thereof comprise at least one asparagine that is replaced by a serine. In one embodiment, the composition comprises at least one antibody or fragment thereof comprises at least one asparagine replaced by a serine. In another embodiment, the composition comprises an antibody or fragment thereof binding to a Tweak molecule, wherein more than about 10%, 5%, 3%, 1%, 0.5%, 0.3%, or 0.1% of the antibodies or fragments thereof comprise at least one asparagine that is replaced by a serine.

The invention also provides a method of producing an amino acid substituted library of a polypeptide of interest comprising: (a) analyzing the primary sequence of the polypeptide of interest to identify the amino acid to be substituted; (b) culturing an eukaryotic cell expressing the polypeptide of interest in media containing a decreased amount of the amino acid to be substituted; and (c) isolating the amino acid substituted polypeptides. In one embodiment, analyzing the polypeptide sequence identifies an amino acid which makes up greater than 3% of the total amino acid content of the polypeptide of interest.

In one embodiment, the amino acid to be substituted is an essential amino acid. In another embodiment, the first amino acid is a non-essential amino acid present in limiting concentrations. In one embodiment, the first amino acid is asparagine. In another embodiment, the second amino acid is serine. In yet another embodiment, the first amino acid is asparagine, and the second amino acid is senile.

In one embodiment, the eukaryotic cell is a mammalian cell. In one embodiment, the mammalian cell is a chinese hamster ovary (CHO), monkey kidney CV1, monkey kidney COS, human lens epithelium, human embryonic kidney, baby hamster kidney, african green monkey kidney, human cervical carcinoma, canine kidney, buffalo rat liver, human lung, human liver, mouse mammary tumor, hybridoma, or myeloma cell lines. In one embodiment, the myeloma cell line is selected from the group consisting of NS0, Sp2/0, and Ag8653.

In one embodiment, the cell is grown on a large scale. In another embodiment, the cell is grown in a bioreactor. In one embodiment, the cell is grown in shaker flasks.

In one embodiment, the polypeptide of interest is selected from the group consisting of: antibody, antibody fragment, enzyme, receptor, hormone, regulatory factor, growth factor, antigen, and binding agent.

The method also provides a method for designing a growth medium for producing a polypeptide of interest comprising: (a) measuring the frequency of essential amino acids, (b) identifying the amino acids that are present at high frequencies, (c) correlating amino acid misincorporation with low amino acid concentration, and (d) supplementing the growth media with the high frequency amino acids, or metabolic precursors thereof. The invention also provides a media produced by the above-described method.

DETAILED DESCRIPTION OF THE INVENTION

Figure 1:
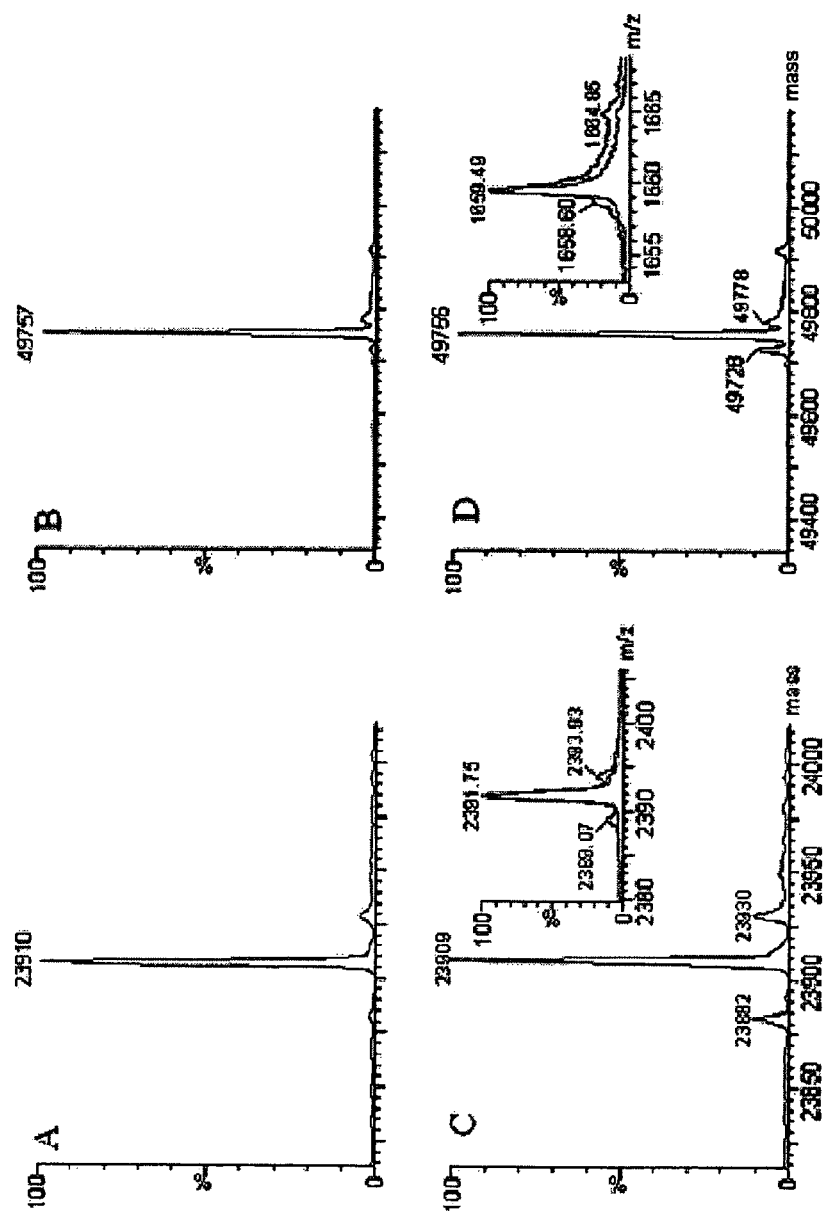
FIG. 1. Deconvoluted mass spectra of the reduced antibody A. A, shown is the light chain of the mAb A-1. B, shown is the heavy chain of the mAb A-1. C, shown is the light chain of a batch from candidate cell line CL 24-34. Inset, shown is the $MH10^{10+}$ peak of the light chain. D, shown is the heavy chain of a batch from candidate cell cline CL24-34. Inset, shown is the $MH30^{30+}$ peak of the heavy chain. The calculated molecular mass for the light chain is 23,910.8 DA; that for the heavy chain is 49,757.2 Da.

The present invention provides methods for the production of proteins and/or polypeptides by cell culture. In particular, the invention provides a method to minimize substitutions of amino acids during translation of a protein/polypeptide of interest. In some embodiments, the invention provides a method of minimizing the substitution of asparagine residues by serine residues by altering the concentration of asparagine, glutamine, and/or serine in the culture media.

The present invention also provides methods for producing an amino acid substituted library of a polypeptide of interest. In some embodiments, cells expressing the protein of interest are grown under conditions, e.g. media having limited amounts of certain amino acids, that result in substitutions being introduced into the protein. The resultant substituted polypeptides can be screened for variant polypeptides that have improved characteristics.

DEFINITIONS

As used herein, the terms "about" and "approximately", as applied to one or more particular cell culture conditions, refer to a range of values that are similar to the stated reference value for that culture condition or conditions. In certain embodiments, the term "about" refers to a range of values that fall within 10 percent or less of the stated reference value for that culture condition or conditions.

The term "amino acid" as used herein refers to any of the twenty naturally occurring amino acids that are normally used in the formation of polypeptides, or analogs or derivatives of those amino acids. Amino acids of the present invention are provided in medium to cell cultures. The amino acids provided in the medium may be provided as salts or in hydrate form.

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

The term "basal media formulation" or "basal media" as used herein refers to any cell culture media used to culture cells that has not been modified either by supplementation, or by selective removal of a certain component.

The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

The term "bioreactor" as used herein refers to any vessel used for the growth of a mammalian cell culture. The bioreactor can be of any size so long as it is useful for the culturing of mammalian cells. Typically, the bioreactor will be at least 1 liter and may be 10, 100, 250, 500, 1000, 2500, 5000, 8000, 10,000, 12,0000 liters or more, or any volume in between. The internal conditions of the bioreactor, including, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or protein of interest. The volume of the large-scale cell culture production bioreactor is typically at least 500 liters and may be 1000, 2000, 2500, 5000, 8000, 10,000, 12,0000 liters or more, or any volume in between. One of ordinary skill in the art will be aware of and will be able to choose suitable bioreactors for use in practicing the present invention.

The term "cell density" as used herein refers to that number of cells present in a given volume of medium.

The terms "culture", "cell culture" and "eukaryotic cell culture" as used herein refer to a eukaryotic cell population that is suspended in a medium (see definition of "medium" below) under conditions suitable to survival and/or growth of the cell population. As will be clear to those of ordinary skill in the art, these terms as used herein may refer to the combination comprising the mammalian cell population and the medium in which the population is suspended.

The term "fed-batch culture" as used herein refers to a method of culturing cells in which additional components are provided to the culture at some time subsequent to the beginning of the culture process. The provided components typically comprise nutritional supplements for the cells which have been depleted during the culturing process. A fed-batch culture is typically stopped at some point and the cells and/or components in the medium are harvested and optionally purified.

"Growth phase" of the cell culture refers to the period of exponential cell growth (the log phase) where cells are generally rapidly dividing. During this phase, cells are cultured for a period of time, usually between 1-4 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. During the growth phase, cells are cultured in nutrient medium containing the necessary additives generally at about 25°-40° C., in a humidified, controlled atmosphere, such that optimal growth is achieved for the particular cell line. Cells are maintained in the growth phase for a period of about between one and four days, usually between two to three days.

"Production phase" of the cell culture refers to the period of time during which cell growth has plateaued. During the production phase, logarithmic cell growth has ended and protein production is primary. During this period of time the medium is generally supplemented to support continued protein production and to achieve the desired glycoprotein product.

The term "expression" or "expresses" are used herein to refer to transcription and translation occurring within a host cell. The level of expression of a product gene in a host cell may be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., Molecular Cloning: A Laboratory Manual, pp. 7.3-7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

The term "hybridoma" as used herein refers to a cell created by fusion of an immortalized cell derived from an immunologic source and an antibody-producing cell. The resulting hybridoma is an immortalized cell that produces antibodies. The individual cells used to create the hybridoma can be from any mammalian source, including, but not limited to, rat, pig, rabbit, sheep, pig, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadramas (See, e.g., Milstein et al., Nature, 537:3053 (1983)).

The terms "medium", "cell culture medium", "culture medium", and "growth medium" as used herein refer to a solution containing nutrients which nourish growing eukaryotic cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. The medium may also be a "defined media"—a serum-free media that contains no proteins, hydrolysates or components of unknown composition. Defined media are free of animal-derived components and all components have a known chemical structure.

The term "perfusion culture" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified.

The terms "polypeptide" or "protein" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit, the terms "polypeptide" and "protein" as used herein are used interchangeably. If discrete functional unit is comprised of more than one polypeptide that physically associate with one another, the term "protein" as used herein refers to the multiple polypeptides that are physically coupled and function together as the discrete unit.

"Recombinantly expressed polypeptide" and "recombinant polypeptide" as used herein refer to a polypeptide expressed from a mammalian host cell that has been genetically engineered to express that polypeptide. The recombinantly expressed polypeptide can be identical or similar to polypeptides that are normally expressed in the mammalian host cell. The recombinantly expressed polypeptide can also foreign to the host cell, i.e. heterologous to peptides normally expressed in the mammalian host cell. Alternatively, the recombinantly expressed polypeptide can be chimeric in that portions of the polypeptide contain amino acid sequences that are identical or similar to polypeptides normally expressed in the mammalian host cell, while other portions are foreign to the host cell.

The term "seeding" as used herein refers to the process of providing a cell culture to a bioreactor or another vessel. The cells may have been propagated previously in another bioreactor or vessel. Alternatively, the cells may have been frozen and thawed immediately prior to providing them to the bioreactor or vessel. The term refers to any number of cells, including a single cell.

The terms "substitution" or "misincorporation" of an amino acid as used herein refer to incorporation of the incorrect amino acid, based on the genetic sequence of the polypeptide, into the sequence of a polypeptide of interest. For example, serine can be misincorporated into a polypeptide sequence at a point in which asparagine is the correct amino acid to be incorporated.

The term "titer" as used herein refers to the total amount of recombinantly expressed polypeptide or protein produced by a mammalian cell culture divided by a given amount of medium volume. Titer is typically expressed in units of milligrams of polypeptide or protein per milliliter of medium.

As used in the present disclosure and claims, the singular forms "a", "an", and "the" include plural forms unless the context clearly dictates otherwise.

It is understood that whenever embodiments are described herein with the language "comprising" otherwise analogous embodiments described in terms of "consisting" and/or "consisting essentially of" are also provided.

Certain Embodiments of the Present Invention

The present invention provides methods for the production of proteins and/or polypeptides by cell culture. In particular, the invention provides a method to minimize substitutions of amino acids during translation of a protein/polypeptide of interest. In one embodiment of the present invention, the cell culture is a batch or fed-batch culture. The methods of the present invention may also be used to control the level of amino acid substitution. For example, substitution of some amino acid residues may actually confer desirable properties on a polypeptide, for example, an antibody. These desirable properties can include, but are not limited to, greater affinity/avidity, and improved in vivo pK. Other embodiments of the invention are discussed in detail below. Those of ordinary skill in the art will understand, however, that various modifications to these preferred embodiments are within the scope of the appended claims. It is the claims and equivalents thereof that define the scope of the present invention, which is not and should not be limited to or by this description of certain preferred embodiments.

Polypeptides

Any polypeptide that is expressible in a host cell may be produced in accordance with the present invention. The polypeptide may be expressed from a gene that is endogenous to the host cell, or from a gene that is introduced into the host cell through genetic engineering. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Polypeptides that may desirably be expressed in accordance with the present invention will often be selected on the basis of an interesting biological or chemical activity. For example, the present invention may be employed to express any pharmaceutically or commercially relevant enzyme, receptor, antibody, hormone, regulatory factor, antigen, binding agent, etc.

Antibodies

Given the large number of antibodies currently in use or under investigation as pharmaceutical or other commercial agents, production of antibodies is of particular interest in accordance with the present invention. Antibodies are proteins that have the ability to specifically bind a particular antigen. Any antibody that can be expressed in a host cell may be used in accordance with the present invention. In one embodiment, the antibody to be expressed is a monoclonal antibody.

Particular antibodies can be made, for example, by preparing and expressing synthetic genes that encode the recited amino acid sequences or by mutating human germline genes to provide a gene that encodes the recited amino acid sequences. Moreover, these antibodies can be produced, e.g., using one or more of the following methods.

Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) Science 228: 1315-1317; WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667,988; and 5,885,793.

In addition to the use of display libraries, other methods can be used to obtain an antibody. For example, a protein (such as TWEAK) or a peptide thereof can be used as an antigen in a non-human animal, e.g., a rodent, e.g., a mouse, hamster, or rat.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) Nature Genetics 7:13-21, U.S. 2003-0070185, WO 96/34096, and WO 96/33735.

In another embodiment, a monoclonal antibody is obtained from the non-human animal, and then modified, e.g., humanized or deimmunized. Winter describes an exemplary CDR-grafting method that may be used to prepare humanized antibodies described herein (U.S. Pat. No. 5,225,539). All or some of the CDRs of a particular human antibody may be replaced with at least a portion of a non-human antibody. It may only be necessary to replace the CDRs required for binding or binding determinants of such CDRs to arrive at a useful humanized antibody that binds to an antigen, such as TWEAK.

Humanized antibodies can be generated by replacing sequences of the Fv variable region that are not directly involved in antigen binding with equivalent sequences from human Fv variable regions. General methods for generating humanized antibodies are provided by Morrison, S. L. (1985) Science 229:1202-1207, by Oi et al. (1986) BioTechniques 4:214, and by U.S. Pat. No. 5,585,089; U.S. Pat. No. 5,693, 761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above, from germline immunoglobulin genes, or from synthetic constructs. The recombinant DNA encoding the humanized antibody can then be cloned into an appropriate expression vector.

Human germline sequences, for example, are disclosed in Tomlinson, I. A. et al. (1992) J. Mol. Biol. 227:776-798; Cook, G. P. et al. (1995) Immunol. Today 16: 237-242; Chothia, D. et al. (1992) J. Mol. Bio. 227:799-817; and Tomlinson et al. (1995) EMBO J. 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs.

Consensus human framework regions can also be used, e.g., as described in U.S. Pat. No. 6,300,064.

A non-human antigen-binding antibody may also be modified by specific deletion of human T cell epitopes or "deimmunization" by the methods disclosed in WO 98/52976 and WO 00/34317. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible, conservative substitutions are made. Often, but not exclusively, an amino acid common to a position in human germline antibody sequences may be used. After the deimmunizing changes are identified, nucleic acids encoding VH and VL can be constructed by mutagenesis or other synthetic methods (e.g., de novo synthesis, cassette replacement, and so forth). A mutagenized variable sequence can, optionally, be fused to a human constant region, e.g., human IgG1 or kappa constant regions.

In some cases, a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs can be eliminated by substitutions outside the CDRs. In some cases, an alteration within a CDR is the only option, and thus variants with and without this substitution can be tested. In other cases, the substitution required to remove a potential T cell epitope is at a residue position within the framework that might be critical for antibody binding. In these cases, variants with and without this substitution are tested. Thus, in some cases several variant deimmunized heavy and light chain variable regions are designed and various heavy/light chain combinations are tested to identify the optimal deimmunized antibody. The choice of the final deimmunized antibody can then be made by considering the binding affinity of the different variants in conjunction with the extent of deimmunization, particularly, the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693,762; 5,693,761; 5,585,089; 5,530,101; and 6,407,213; Tempest et al. (1991) Biotechnology 9:266-271. Still another method is termed "humaneering" and is described, for example, in U.S. 2005-008625.

The antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237. Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. Antibodies may also have mutations that stabilize the disulfide bond between the two heavy chains of an immunoglobulin, such as mutations in the hinge region of IgG4, as disclosed in the art (e.g., Angal et al. (1993) Mol. Immunol. 30:105-08). See also, e.g., U.S. 2005-0037000.

Affinity Maturation. In one embodiment, an antibody is modified, e.g., by mutagenesis, to provide a pool of modified antibodies. The modified antibodies are then evaluated to identify one or more antibodies which have altered functional properties (e.g., improved binding, improved stability, reduced antigenicity, or increased stability in vivo). In one implementation, display library technology is used to select or screen the pool of modified antibodies. Higher affinity antibodies are then identified from the second library, e.g., by using higher stringency or more competitive binding and washing conditions. Other screening techniques can also be used.

In some implementations, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particularly within 10, 5, or 3 amino acids of a CDR junction. In the case of antibodies, mutagenesis can also be limited to one or a few of the CDRs, e.g., to make step-wise improvements.

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity, relative to the donor non-human antibody. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations, more than one or two germline sequences are used, e.g., to form a consensus sequence.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) CRC Crit. Rev. Biochem. 22:259-306. Removal of any carbohydrate moieties present on the antibodies may be accomplished chemically or enzymatically as described in the art (Hakimuddin et al. (1987) Arch. Biochem. Biophys. 259:52; Edge et al. (1981) Anal. Biochem. 118:131; and Thotakura et al. (1987) Meth. Enzymol. 138: 350). See, e.g., U.S. Pat. No. 5,869,046 for a modification that increases in vivo half life by providing a salvage receptor binding epitope.

The antibodies can be in the form of full length antibodies, or in the form of fragments of antibodies, e.g., Fab, F(ab')$_2$, Fd, dAb, and scFv fragments. Additional forms include a protein that includes a single variable domain, e.g., a camel or camelized domain. See, e.g., U.S. 2005-0079574 and Davies et al. (1996) Protein Eng. 9(6):531-7.

In one embodiment, the methods of the invention are used to produce an antibody that specifically binds a tumor-necrosis factor (TNF)-related cytokines superfamily member. TNF-related cytokines are proteins that have an array of functions, including ones implicated in immune regulation and apoptosis regulation. TWEAK (TNF-like weak inducer of apoptosis) is one member of this superfamily. Examples of TWEAK sequences can be readily found in sequence databases, and include, but are not limited to, for example GenBank Accession Number BAE16557 (SEQ ID NO:4). Examples of anti-TWEAK antibodies are described in WO 2006/130374 and US Appl. Pub. No. 2008/0241163 which are herein incorporated by reference. In one embodiment, the anti-TWEAK antibody is the humanized antibody huP2D10. huP2D10 comprises the heavy chain (SEQ ID NO:1) and light chain (SEQ ID NOs: 2 or 3) variable amino acid sequences described below:

```
huP2D10 H1 IgG1 heavy chain:
                                                                         (SEQ ID NO: 1)
EVQLVESGGGLVQPGGSLRLSCAASGFTFSRYAMSWVRQAPGKGLEWVAEISSGGSYPYYP

DTVTGRFTISRDNAKNSLYLQMNSLRAEDTAVYYCARVLYYDYDGDRIEVMDYWGQGTLV

TVSSASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGNVFS

CSVMHEALHNHYTQKSLSLSPG huP2D10 L1 light chain:
                                                                         (SEQ ID NO: 2)
DVVMTQSPLSLPVTPGEPASISCRSSQSLVSSKGNTYLHWYLQKPGQSPQFLIYKVSNRFSGV

PDRFSGSGSGTDFTLKISRVEAEDVGVYFCSQSTHFPRTFGGGTKVEIKRTVAAPSVFIFPPSDE

QLKSGTASVVCLLNNFYPREAKVQWKVDNALQSGNSQESVTEQDSKDSTYSLSSTLTLSKA

DYEKHKVYACEVTHQGLSSPVTKSFNRGEC huP2D10 L2 light chain:
                                                                         (SEQ ID NO: 3)
DVVMTQSPLSLPVTPGEPASISCRSSQSLVSSKGNTYLHWYLQKPGQSPQLLIYKVSNRFSGV

PDRFSGSGSGTDFTLKISRVEAEDVGVYYCSQSTHFPRTFGGGTKVE1KRTVAAPSVFIFPPSD

EQLKSGTASVVCLLNNFYPREAKVQWKVDNALQSGNSQESVTEQDSKDSTYSLSSTLTLSKA

DYEKHKVYACEVTHQGLSSPVTKSFNRGEC

Human TWEAK amino acid sequence:
                                                                         (SEQ ID NO: 4)
MAARRSQRRRGRRGEPGTALLVPLALGLGLALACLGLLLAVVSLGSRASLSAQEPAQEELVAEEDQDPSELNPQTEES QDPAPFLNRLVRPRRSAPKGRKTRARRAIAAHYEVHPRPGQDGAQAGVDGTVSGWEEARINSSSPLRYNRQIGEFIVTR
```

-continued

AGLYYLYCQVHFDEGKAVYLKLDLLVDGVLALRCLEEFSATAASSLGPQLRLCQVSGLLALRPGSSLRIRTLPWAHLK

AAPFLTYFGLFQVH

In one embodiment, the invention provides a protein that includes a first and a second immunoglobulin variable domain sequence and that binds to TWEAK, e.g., human TWEAK. The protein can bind to TWEAK, e.g., with an affinity corresponding to a $K_D$ of less than $10^{-7}$ M, e.g., $10^{-8}$, $10^{-9}$, $10^{-10}$, $10^{-11}$ M or better. The protein is also referred to herein as an "anti-TWEAK antibody." The first and second immunoglobulin variable domain sequences can include at least a sufficient portion of an immunoglobulin variable domain to form an antigen binding site that binds to TWEAK. Typically, the first and second immunoglobulin variable domain sequences correspond to immunoglobulin variable domain sequences of a heavy and light chain, respectively, e.g., a paired or otherwise compatible heavy and light chain.

The antibody can bind to an epitope on TWEAK which includes at least one, two, three or four amino acid residues from an epitope on TWEAK recognized by P2D10, to a peptide from TWEAK that is bound by P2D10 (e.g., a peptide less than 25, 20, or 15 amino acids in length) or to a region of TWEAK recognized by P2D10. For example, the antibody specifically binds to an epitope, e.g., a linear or a conformational epitope, of TWEAK, in particular human TWEAK, e.g., the soluble region of TWEAK. The antibody may compete with P2D10 for binding to TWEAK, e.g., to human TWEAK. The antibody may competitively inhibit binding of P2D10 to TWEAK, e.g., human TWEAK. In one embodiment, the antibody may bind to an epitope which overlaps with that of P2D10, e.g., includes at least one, two, three or four amino acids in common with the P2D10 epitope, or an epitope which, when bound, sterically prevents TWEAK interaction with P2D10.

For example, the anti-TWEAK antibody can bind to TWEAK and modulate, e.g., inhibit, an interaction (e.g., binding) between TWEAK and a TWEAK receptor, e.g., Fn14 (e.g., human Fn14). The antibody may also reduce signaling activity of a TWEAK receptor. The antibody may target TWEAK, sequester TWEAK, and/or modulate the in vivo stability of TWEAK.

In one embodiment, the antibody specifically binds to at least a part of the interaction site on TWEAK that contacts Fn14 (e.g., human Fn14). The antibody may compete with Fn14 for binding to TWEAK, e.g., to human TWEAK. The antibody may competitively inhibit binding of Fn14 to TWEAK. The antibody may interact with an epitope on TWEAK which, when bound, sterically prevents interaction between TWEAK and Fn14 (e.g., between human TWEAK and human Fn14).

In one embodiment, the antibody can inhibit one or more TWEAK-associated activities with an $IC_{50}$ of about 50 nM to 5 pM, typically about 100 to 250 pM or less. For example, the antibody can inhibit the ability of TWEAK to promote endothelial cell proliferation or neovascularization. In one embodiment, the anti-TWEAK antibody reduces at least one TWEAK-associated activity, e.g., such that the antibody can modulate an inflammatory condition when administered to a subject.

In other embodiments, the antibody can associate with TWEAK with kinetics in the range of $10^3$ to $10^8$ M$^{-1}$ s$^{-1}$, typically $10^4$ to $10^7$ M$^{-1}$ s$^{-1}$. In yet another embodiment, the antibody has dissociation kinetics in the range of $10^{-2}$ to $10^{-6}$ s$^{-1}$, typically $10^{-2}$ to $10^{-5}$ s$^{-1}$. In one embodiment, the antibody binds to TWEAK, e.g., human TWEAK, with an affinity and/or kinetics similar to (e.g., within a factor of five or ten of) monoclonal antibody P2D10, or modified forms thereof, e.g., chimeric forms or humanized forms thereof (e.g., a humanized form described herein). The affinity and binding kinetics of the anti-TWEAK antibody can be tested, e.g., using biosensor technology (BIACORE™).

In one embodiment, the antibody is an antigen-binding fragment of a full length antibody, e.g., a Fab, F(ab)2, Fv or a single chain Fv fragment. Typically, the antibody is a full length antibody. The antibody can be a monoclonal antibody or a mono-specific antibody. For example, the antibody is in a composition that includes less than 20 other species of anti-TWEAK antibodies, e.g., in a composition that does not include another species of anti-TWEAK antibody.

The antibody can be effectively human. An "effectively human" antibody is an antibody that includes a sufficient number of human amino acid positions such that the antibody does not elicit an immunogenic response in a normal human. Preferably, the protein does not evoke a neutralizing antibody response, e.g., the human anti-murine antibody (HAMA) response. HAMA can be problematic in a number of circumstances, e.g., if the antibodies are desired to be administered repeatedly, e.g., in treatment of a chronic or recurrent disease condition. A HAMA response can make repeated antibody administration potentially ineffective because of an increased antibody clearance from the serum (see, e.g., Saleh et al., Cancer Immunol. Immunother., 32:180-190 (1990)) and also because of potential allergic reactions (see, e.g., LoBuglio et al. (1986) Hybridoma, 5:5117-5123).

For example, the antibody can be a human, humanized, CDR-grafted, chimeric, mutated, affinity matured, deimmunized, synthetic or otherwise in vitro-generated antibody, and combinations thereof. In one embodiment, the anti-TWEAK antibody is a humanized antibody.

The heavy and light chains of the anti-TWEAK antibody can be substantially full-length. The protein can include at least one, and preferably two, complete heavy chains, and at least one, and preferably two, complete light chains) or can include an antigen-binding fragment (e.g., a Fab, F(ab')2, Fv or a single chain Fv fragment). In yet other embodiments, the antibody has a heavy chain constant region chosen from, e.g., IgG1, IgG2, IgG3, IgG4, IgM, IgA1, IgA2, IgD, and IgE; particularly, chosen from, e.g., IgG1, IgG2, IgG3, and IgG4, more particularly, IgG1 (e.g., human IgG1). Typically, the heavy chain constant region is human or a modified form of a human constant region. In another embodiment, the antibody has a light chain constant region chosen from, e.g., kappa or lambda, particularly, kappa (e.g., human kappa).

Receptors

Another class of polypeptides that have been shown to be effective as pharmaceutical and/or commercial agents includes receptors. Receptors are typically trans-membrane glycoproteins that function by recognizing an extra-cellular signaling ligand. Receptors typically have a protein kinase domain in addition to the ligand recognizing domain, which initiates a signaling pathway by phosphorylating target intracellular molecules upon binding the ligand, leading to developmental or metabolic changes within the cell. In one embodiment, the receptors of interest are modified so as to remove the transmembrane and/or intracellular domain(s), in place of which there may optionally be attached an Ig-domain. In one embodiment, receptors to be produced in accordance with the present invention are receptor tyrosine kinases (RTKs). The RTK family includes receptors that are crucial for a variety of functions numerous cell types (see, e.g., Yarden and Ullrich, Ann. Rev. Biochem. 57:433-478, 1988; Ullrich and Schlessinger, Cell 61:243-254, 1990, incorporated herein by reference). Non-limiting examples of RTKs include members of the fibroblast growth factor (FGF) receptor family, members of the epidermal growth factor receptor (EGF) family, platelet derived growth factor (PDGF) receptor, tyrosine kinase with immunoglobulin and EGF homology domains-1 (TIE-1) and TIE-2 receptors (Sato et al., Nature 376(6535):70-74 (1995), incorporated herein be reference) and c-Met receptor, some of which have been suggested to promote angiogenesis, directly or indirectly (Mustonen and Alitalo, J. Cell Biol. 129:895-898, 1995). Other non-limiting examples of RTK's include fetal liver kinase 1 (FLK-1) (sometimes referred to as kinase insert domain-containing receptor (KDR) (Terman et al., Oncogene 6:1677-83, 1991) or vascular endothelial cell growth factor receptor 2 (VEGFR-2)), fms-like tyrosine kinase-1 (Flt-1) (DeVries et al. Science 255; 989-991, 1992; Shibuya et al., Oncogene 5:519-524, 1990), sometimes referred to as vascular endothelial cell growth factor receptor 1 (VEGFR-1), neuropilin-1, endoglin, endosialin, and Ax1. Those of ordinary skill in the art will be aware of other receptors that can preferably be expressed in accordance with the present invention.

Growth Factors and Other Signaling Molecules

Another class of polypeptides that have been shown to be effective as pharmaceutical and/or commercial agents includes growth factors and other signaling molecules. Growth factors are typically glycoproteins that are secreted by cells and bind to and activate receptors on other cells, initiating a metabolic or developmental change in the receptor cell.

Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (TLs), e.g., IL-1 to IL-10; tumor necrosis factor (TNF) alpha and beta; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta. One of ordinary skill in the art will be aware of other growth factors or signaling molecules that can be expressed in accordance with the present invention.

G-Protein Coupled Receptors

Another class of polypeptides that have been shown to be effective as pharmaceutical and/or commercial agents includes growth factors and other signaling molecules. G-protein coupled receptors (GPCRs) are proteins that have seven transmembrane domains. Upon binding of a ligand to a GPCR, a signal is transduced within the cell which results in a change in a biological or physiological property of the cell.

GPCRs, along with G-proteins and effectors (intracellular enzymes and channels which are modulated by G-proteins), are the components of a modular signaling system that connects the state of intracellular second messengers to extracellular inputs. These genes and gene-products are potential causative agents of disease.

The GPCR protein superfamily now contains over 250 types of paralogues, receptors that represent variants generated by gene duplications (or other processes), as opposed to orthologues, the same receptor from different species. The superfamily can be broken down into five families: Family I, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cAMP receptor family, important in the chemotaxis and development of *D. discoideum*; and Family V, the fungal mating pheromone receptors such as STE2.

Cells

Any mammalian cell or cell type susceptible to cell culture, and to expression of polypeptides, may be utilized in accordance with the present invention. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells ±DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL 51); TR1 cells (Mather et al., Annals N.Y. Acad. Sci., 383: 44-68 (1982)); MRC 5 cells; FS4 cells; and a human hepatoma line (Hep G2). In one embodiment, the present invention is used in the culturing of and expression of polypeptides from CHO cell lines.

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

As noted above, in many instances the cells will be selected or engineered to produce high levels of protein or polypeptide. Often, cells are genetically engineered to produce high levels of protein, for example by introduction of a gene encoding the protein or polypeptide of interest and/or by introduction of control elements that regulate expression of the gene (whether endogenous or introduced) encoding the polypeptide of interest.

Media

The mammalian cell culture of the present invention is prepared in any medium suitable for the particular cell being cultured. Commercially available media such as Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions. In addition, any of the media described in Ham and Wallace, (1979) Meth. Enz., 58:44; Barnes and Sato, (1980) Anal. Biochem., 102:255; U.S. Pat. No. 4,767,704; 4,657,866; 4,927,762; 5,122,469 or 4,560,655; International Publication Nos. WO 90/03430; and WO 87/00195; the disclosures of all of which are incorporated herein by reference, may be used as culture media. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and their suitable carriers, and glucose or an equivalent energy source. Any other necessary supplements may also be included at appropriate concentrations that would be known to those skilled in the art.

In one embodiment, the media is supplemented with amino acids, or metabolic precursors of those amino acids in amounts sufficient to reduce amino acid substitution. The amino acids can be essential amino acids. The essential amino acids can act as precursors to other amino acids utilized by the cell. Examples of essential amino acids, includes but is not limited to, arginine, histidine, isoleucine, leucine, lysine, methionine, phenylalanine, threonine, tryptophan, and valine. In some embodiments, the media is supplemented with asparagine or glutamine.

The amount of supplementation required can vary depending on the cellular growth conditions. For example, factors that influence cellular consumption rates, will affect the amount of supplementation that is required to prevent substitution. Such factors include, but are not limited to, temperature, osmolarity, and pH. For example, to reduce the consumption rate, osmolarity of the cell culture medium is maintained at or close to physiological levels. In one embodiment, temperature is reduced during production of the protein of interest. In addition, factors that affect ammonia or lactic acid levels in a culture will also affect the amount of supplementation that is necessary.

In one embodiment, the mammalian host cell is a CHO cell and a suitable medium contains a basal medium component such as a DMEM/HAM F-12 based formulation (for composition of DMEM and HAM F12 media, see culture media formulations in American Type Culture Collection Catalogue of Cell Lines and Hybridomas, Sixth Edition, 1988, pages 346-349) with modified concentrations of some components such as amino acids, salts, sugar, and vitamins, and optionally containing glycine, hypoxanthine, and thymidine; recombinant human insulin, hydrolyzed peptone, such as Primatone HS or Primatone RL (Sheffield, England), or the equivalent; a cell protective agent, such as Pluronic F68 or the equivalent pluronic polyol; gentamycin; and trace elements.

Cell Culture Phase

Various methods of preparing mammalian cells for production of proteins or polypeptides by batch and fed-batch culture are well known in the art. A nucleic acid sufficient to achieve expression (typically a vector containing the gene encoding the polypeptide or protein of interest and any operably linked genetic control elements) may be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbentassay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Once a cell that expresses the polypeptide or protein of interest has been identified, the cell is propagated in culture by any of the variety of methods well-known to one of ordinary skill in the art. The cell expressing the polypeptide of interest is typically propagated by growing it at a temperature and in a medium that is conducive to the survival, growth and viability of the cell. The initial culture volume can be of any size, but is often smaller than the culture volume of the production bioreactor used in the final production of the polypeptide or protein of interest, and frequently cells are passaged several times in bioreactors of increasing volume prior to seeding the production bioreactor. The cell culture can be agitated or shaken to increase oxygenation of the medium and dispersion of nutrients to the cells. Alternatively or additionally, special sparging devices that are well known in the art can be used to increase and control oxygenation of the culture. In accordance with the present invention, one of ordinary skill in the art will understand that it can be beneficial to control or regulate certain internal conditions of the bioreactor, including but not limited to pH, temperature, oxygenation, etc.

The cell density useful in the methods of the present invention can be chosen by one of ordinary skill in the art. In accordance with the present invention, the cell density can be as low as a single cell per culture volume. In some embodiments of the present invention, starting cell densities can range from about $2 \times 10^2$ viable cells per mL to about $2 \times 10^3$, $2 \times 10^4$, $2 \times 10^5$, $2 \times 10^6$, $5 \times 10^6$ or $10 \times 10^6$ viable cells per mL and higher.

In accordance with the present invention, the culture size can be any volume that is appropriate for production of polypeptides. In one embodiment, the volume of the production bioreactor is at least 500 liters. In other preferred embodiments, the volume of the production bioreactor is 1000, 2000, 2500, 5000, 8000, 10,000, 12,000 liters or more, or any volume in between. One of ordinary skill in the art will be aware of and will be able to choose a suitable culture size for use in practicing the present invention. The production bioreactor may be constructed of any material that is conducive to cell growth and viability that does not interfere with expression or stability of the produced polypeptide or protein.

The temperature of the cell culture will be selected based primarily on the range of temperatures at which the cell culture remains viable. For example, during the initial growth phase, CHO cells grow well at 37° C. In general, most mammalian cells grow well within a range of about 25° C. to 42° C.

In one embodiment of the present invention, the temperature of the initial growth phase is maintained at a single, constant temperature. In another embodiment, the temperature of the initial growth phase is maintained within a range of temperatures. For example, the temperature may be steadily increased or decreased during the initial growth phase. Alternatively, the temperature may be increased or decreased by discrete amounts at various times during the initial growth phase. One of ordinary skill in the art will be able to determine whether a single or multiple temperatures should be used, and whether the temperature should be adjusted steadily or by discrete amounts.

The cells may be grown during the initial growth phase for a greater or lesser amount of time, depending on the needs of the practitioner and the requirement of the cells themselves. In one embodiment, the cells are grown for a period of time sufficient to achieve a viable cell density that is a given percentage of the maximal viable cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more. The cells would be grown for 0 days in the production bioreactor if their growth in a seed bioreactor, at the initial growth phase temperature, was sufficient that the viable cell density in the production bioreactor at the time of its inoculation is already at the desired percentage of the maximal viable cell density. The practitioner of the present invention will be able to choose the duration of the initial growth phase depending on polypeptide or protein production requirements and the needs of the cells themselves.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

In one embodiment, at the end of the initial growth phase, at least one of the culture conditions can be shifted so that a second set of culture conditions is applied. The shift in culture conditions can be accomplished by a change in the temperature, pH, osmolality or chemical inductant level of the cell culture. In one embodiment, the culture conditions are shifted by shifting the temperature of the culture.

When shifting the temperature of the culture, the temperature shift may be relatively gradual. For example, it may take several hours or days to complete the temperature change. Alternatively, the temperature shift may be relatively abrupt. For example, the temperature change may be complete in less than several hours. Given the appropriate production and control equipment, such as is standard in the commercial large-scale production of polypeptides or proteins, the temperature change may even be complete within less than an hour.

The temperature of the cell culture in the subsequent growth phase will be selected based primarily on the range of temperatures at which the cell culture remains viable and expresses recombinant polypeptides or proteins at commercially adequate levels. In general, most mammalian cells remain viable and express recombinant polypeptides or proteins at commercially adequate levels within a range of about 25° C. to 42° C. Preferably, mammalian cells remain viable and express recombinant polypeptides or proteins at commercially adequate levels within a range of about 25° C. to 35° C. Those of ordinary skill in the art will be able to select appropriate temperature or temperatures in which to grow cells, depending on the needs of the cells and the production requirements of the practitioner.

In accordance with the present invention, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture may be shifted by shifting one or more of a number of culture conditions including, but not limited to, temperature, pH, osmolality, and sodium butyrate levels. In one embodiment, the temperature of the culture is shifted. According to this embodiment, during the subsequent production phase, the culture is maintained at a temperature or temperature range that is lower than the temperature or temperature range of the initial growth phase. For example, during the subsequent production phase, CHO cells express recombinant polypeptides and proteins well within a range of 25° C. to 35° C.

In accordance with the present invention, the cells may be maintained in the subsequent production phase until a desired cell density or production titer is reached. In one embodiment, the cells are maintained in the subsequent production phase until the titer to the recombinant polypeptide or protein reaches a maximum. In other embodiments, the culture may be harvested prior to this point, depending on the production requirement of the practitioner or the needs of the cells themselves. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it may be desirable to allow the viable cell density to reach a maximum, and then allow the viable cell density to decline to some level before harvesting the culture. In an extreme example, it may be desirable to allow the viable cell density to approach or reach zero before harvesting the culture.

In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells may be grown for 1, 2, 3, 4, 5, 6, 7, 8, 9, 10, 11, 12, 13, 14, 15, 16, 17, 18, 19, 20 or more days. In some cases, the cells may be allowed to grow for a month or more. The practitioner of the present invention will be able to choose the duration of the subsequent production phase depending on polypeptide or protein production requirements and the needs of the cells themselves.

In certain cases, it is beneficial or necessary to decrease certain components of the cell culture media during the growth and/or subsequent production phase. In certain embodiments, the concentration of particular amino acids is reduced in the culture media compared to the standard growth media so that the level of misincorporation of amino acids is minimized. In one embodiment, the amount of serine is reduced in the culture media.

In certain cases, an increased concentration of the amino acids can be added in the basal media or else supplemented in the feed media for a fed-batch system.

In certain cases, it may be beneficial or necessary to supplement the cell culture during the growth and/or subsequent production phase with nutrients or other medium components that have been depleted or metabolized by the cells. For example, it might be advantageous to supplement the cell culture with nutrients or other medium components observed to have been depleted. Alternatively or additionally, it may be beneficial or necessary to supplement the cell culture prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

In one embodiment, the method comprises cultivating cells and monitoring the level of amino acids in the culture media. In one embodiment, monitoring is during the growth phase of the cell culture. In certain embodiments, an amino acid is added to the culture if the level of that amino acid is essentially depleted in the culture medium. A medium that is "essentially depleted" in one amino acid refers to a medium in which the level (or concentration) of the amino acid is below the level of detection. In one embodiment, a medium is "essentially depleted" in asparagine when the level of asparagine is below detectable levels as measured by HPLC or GC-MS, for example at or lower than about 100 µM based on HPLC analysis.

In certain embodiments, in addition to supplementing a culture with one or more amino acids, the temperature of the culture is decreased.

In some embodiments, amino acids are added to the culture. In certain embodiments, the amino acid asparagine is added to the culture. In another embodiment, the amino acid glutamine is added to the culture. The amount of the amino acids added to the culture can vary depending on the cell being grown, or other conditions. One of ordinary skill in the art can readily determine the optimal concentration of the amino acid to add to the culture. Not to be considered limiting, but in certain embodiments, the amount of asparagine or glutamine is greater than 0.1 mM. In further embodiments, the amount of asparagine or glutamine added to the culture is between about 1 mM to about 10 mM. In another embodiment, the amount of asparagine or glutamine added to the culture is between about 1 mM to about 6 mM. In another embodiment, the amount of asparagine or glutamine is about 3 mM. In yet another embodiment, the amount of asparagine or glutamine is about 6 mM.

The invention provides methods for preparing an anti-Tweak antibody, e.g., an antibody comprising one or more of the CDRs or the variable regions set forth in SEQ ID NOs: 1, 2 or 3, such as an antibody comprising or consisting of the heavy chain set forth in SEQ ID NO: 1 and the light chain set forth in SEQ ID NO: 3. An anti-Tweak antibody may also be an antibody having at least about 90%, 95%, 98%, or 99% amino acid sequence identity in one or more CDRs and/or in the whole variable light or variable domains. In one embodiment, the method comprises providing a growth medium containing more than about 1, 2, 3, 4, 5, or 6 mM Asparagine. In one embodiment, the method comprises providing a feed medium containing more than about 1, 2, 3, 4, 5, or 6 g/L Asparagine. In one embodiment, the concentration of Asparagine in the feed medium is about 3-8 g/L. In one embodiment, the concentration of Asparagine in the growth medium is about 3-6 mM. In one embodiment, the method comprises providing a growth medium containing between about 1 and 6 mM asparagine and providing a feed medium containing about 3-8 g/L of asparagine at a frequency and level such that the amount of asparagine does not fall below detectable levels during growth phase. In one embodiment, the method comprises culturing the cells at about 28° C. with a total amount of Asparagine added at less than 1 g/L. Cells may also be cultured at their regular temperature, e.g., around 36 or 37° C., and when a large amount of cells have been obtained, the temperature is reduced to lower levels to reduce misincorporation. In one embodiment, cells are grown at a temperature that is about 1 or 2° C. lower than their optimized (or usual) growth temperature. For example, cells may be cultured through the entire growth process, i.e, from inoculation on, at about 35° C. to reduce or essentially eliminate amino acid misincorporations.

These supplementary components, including the amino acids, may all be added to the cell culture at one time, or they may be provided to the cell culture in a series of additions. In one embodiment of the present invention, the supplementary components are provided to the cell culture at multiple times in proportional amounts. In another embodiment, it may be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the medium or solution containing the supplementary components added to the cell culture may be 1, 2, 3, 4, 5, 6, 7, 8, 9, 10, 15, 20, 25, 30, 35, 40, 45 or 50% of the volume of the cell culture prior to providing the supplementary components.

The cell culture may be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc. For example, pH can be controlled by supplying an appropriate amount of acid or base and oxygenation can be controlled with sparging devices that are well known in the art.

In certain embodiments of the present invention, the practitioner may find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase. In order to monitor certain cell culture conditions, it will be necessary to remove small aliquots of the culture for analysis. One of ordinary skill in the art will understand that such removal may potentially introduce contamination into the cell culture, and will take appropriate care to minimize the risk of such contamination.

As non-limiting example, it may be beneficial or necessary to monitor temperature, pH, cell density, cell viability, integrated viable cell density, lactate levels, ammonium levels, osmolarity, or titer of the expressed polypeptide or protein. Numerous techniques are well known in the art that will allow one of ordinary skill in the art to measure these conditions. For example, cell density may be measured using a hemacytometer, a Coulter counter, or Cell density examination (CE-DEX). Viable cell density may be determined by staining a culture sample with Trypan blue. Since only dead cells take up the Trypan blue, viable cell density can be determined by counting the total number of cells, dividing the number of cells that take up the dye by the total number of cells, and taking the reciprocal. HPLC can be used to determine the levels of lactate, ammonium or the expressed polypeptide or protein. Alternatively, the level of the expressed polypeptide or protein can be determined by standard molecular biology techniques such as coomassie staining of SDS-PAGE gels, Western blotting, Bradford assays, Lowry assays, Biuret assays, and UV absorbance. It may also be beneficial or necessary to monitor the post-translational modifications of the expressed polypeptide or protein, including phosphorylation and glycosylation.

Isolation of Expressed Polypeptide

In general, it will typically be desirable to isolate and/or purify proteins or polypeptides expressed according to the present invention. In one embodiment, the expressed polypeptide or protein is secreted into the medium and thus cells and other solids may be removed, as by centrifugation or filtering for example, as a first step in the purification process. Alternatively, the expressed polypeptide can be bound to the surface of the host cell. In this embodiment, the media is removed and the host cells expressing the polypeptide or protein are lysed as a first step in the purification process. Lysis of mammalian host cells can be achieved by any number of means well known to those of ordinary skill in the art, including physical disruption by glass beads and exposure to high pH conditions.

The polypeptide can be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

Pharmaceutical Compositions

A polypeptide (for example an antibody such as an anti-TWEAK antibody described herein) can be formulated as a pharmaceutical composition for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) J. Pharm. Sci. 66:1-19).

Pharmaceutical formulation is a well-established art, and is further described, e.g., in Gennaro (ed.), Remington. The Science and Practice of Pharmacy, $20^{th}$ ed., Lippincott, Williams & Wilkins (2000) (ISBN: 0683306472); Ansel et al., Pharmaceutical Dosage Forms and Drug Delivery Systems, $7^{th}$ Ed., Lippincott Williams & Wilkins Publishers (1999) (ISBN: 0683305727); and Kibbe (ed.), Handbook of Pharmaceutical Excipients American Pharmaceutical Association, $3^{rd}$ ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

In one embodiment, the antibody is formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the polypeptide may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

A polypeptide, such as anti-TWEAK antibody can be modified, e.g., with a moiety that improves its stabilization and/or retention in circulation, e.g., in blood, serum, or other tissues, e.g., by at least 1.5, 2, 5, 10, or 50 fold. For example, the anti-TWEAK antibody can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, the anti-TWEAK antibody can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

In some implementations, the polypeptide or antibody can also be coupled to or otherwise associated with a label or other agent, e.g., another therapeutic agent such as a cytotoxic or cytostatic agent, although, in many embodiments, this configuration is unnecessary. Examples of cytotoxic and chemotherapeutic agents include taxol, cytochalasin B, gramicidin D, vinblastine, doxorubicin, daunorubicin, a maytansinoid (e.g., maytansinol or the DM1 maytansinoid, a sulfhydryl-containing derivative of maytansine), mitoxantrone, mithramycin, actinomycin D, 1-dehydrotestosterone, glucocorticoids, procaine, taxane, tetracaine, lidocaine, propranolol, and puromycin and analogs or homologs thereof.

When the polypeptide or antibody is used in combination with a second agent (e.g., an anti-TNF-α antibody or other agent), the two agents can be formulated separately or together. The agents can be formulated or otherwise used in a synergistically effective amount. It is also possible to use one or both of the agents in amounts less than would be used for mono-therapy. For example, the respective pharmaceutical compositions can be mixed, e.g., just prior to administration, and administered together or can be administered separately, e.g., at the same or different times.

The foregoing description is to be understood as being representative only and is not intended to be limiting. Alternative methods and materials for implementing the invention and also additional applications will be apparent to one of skill in the art, and are intended to be included within the accompanying claims.

EXAMPLES

A recombinant monoclonal antibody produced by CHO cell fed-batch culture was found to have amino acid sequence substitution upon analysis by intact mass and peptide mapping mass spectrometry. Sequence analysis of the gene construct revealed no genetic basis. A detailed analysis revealed that multiple sites for asparagine were being randomly substituted by serine, pointing to mistranslation as the likely source. Results from time course analysis of cell culture suggest that misincorporation was occurring midway through the fed-batch process, and was correlated to asparagine reduction to below detectable levels in the culture. Separate shake flask experiments were carried out that confirmed starvation of asparagine and not excess of serine in the medium as the root cause of the phenomenon. Maintenance of asparagine at low levels in 2 L bench-scale culture via controlled supplementation of asparagine-containing feed eliminated the occurrence of misincorporation. This strategy was implemented in a clinical manufacturing process and scaled up successfully to the 200L and 2000L bioreactor scales.

Example 1

Misincorporation of amino acids in proteins expressed in *Escherichia coli* has been well documented but not in proteins expressed in mammalian cells under normal recombinant protein production conditions. Here we report for the first time that Ser can be incorporated at Asn positions in proteins expressed in Chinese hamster ovary cells. This misincorporation was discovered as a result of intact mass measurement, peptide mapping analysis, and tandem mass spectroscopy sequencing. Our analyses showed that the substitution was not related to specific protein molecules or DNA codons and was not site-specific. We believe that the incorporation of Ser at sites coded for Asn was due to mischarging of tRNAAsn rather than to codon misreading. The rationale for substitution of Asn by Ser and not by other amino acids is also discussed. Further investigation indicated that the substitution was due to the starvation for Asn in the cell culture medium and that the substitution could be limited by using the Asn-rich feed. These observations demonstrate that the quality of expressed proteins should be closely monitored when altering cell culture conditions.

Introduction

Many recombinant proteins have been approved as therapeutic drugs by the Food and Drug Administration, and many more are undergoing clinical trial (1). For economic and practical reasons, considerable effort has been made to increase product yield and process efficiency for proteins made in mammalian cell culture. Nowadays, large amounts of proteins can be expressed efficiently in optimized expression systems, with yields from bioreactors having improved more than 100-fold during the past two decades (2). Yields as high as 10 g/liter have been reported for production of monoclonal antibodies in CHO2 cells (3). These yields are due mainly to improvements in host cell engineering, cell line selection, and culture medium optimization (4). However, it is well known that overexpressing recombinant proteins can lead to nutritional stresses in the host cells and that these stresses can markedly increase the frequency of random translational errors, resulting in a heterogeneous mixture of proteins (5-11). A variety of translational errors have been observed during overexpression of proteins in *Escherichia coli*, including frame shifts, premature truncation, read-through, leaky stop codons, and amino acid misincorporation (12-16). Nevertheless, there are few such reports for proteins made in mammalian cells, and it is commonly believed that the fidelity of translation in mammalian cells is higher (8, 17). Here we report for the first time that misincorporation, namely of Ser for Asn, can occur in proteins overexpressed in CHO cells under normal recombinant protein production conditions. Further investigation showed that supplementation of the medium with Asn can overcome this problem. Our work demonstrates that protein products should be closely monitored for misincorporation, for example, by molecular mass determination and peptide mapping during optimization of culture conditions.

Experimental Procedures

Protein Expression—Proteins were expressed in CHO cells cultured in 125-ml, 1-liter, and 3-liter shake flasks or 5-liter bioreactors. The cultures were grown in proprietary medium supplemented with feeds containing additives described under "Investigation of the cause of the Asn→Ser substitution section" and Table 2. The process was carried out at a temperature of 35-37° C. or at 37° C. with a subsequent change to 28° C. on the third day. For bioreactors, the pH was maintained at neutrality by the addition of 1 M sodium carbonate and by sparging with CO2. Dissolved oxygen was controlled at 30% air saturation. Cell viability was determined by the trypan blue exclusion method, and viable cell density was determined using a Cedex instrument (Innovatis, Bielefeld, Germany). The conditioned medium samples were harvested at the indicated time points.

Protein Purification—Antibody A and its mutants were purified by chromatography using HiTrap rProtein A FF GE followed by size exclusion chromatography on a Superdex 200 column (GE Healthcare). Antibody B was purified on protein A-Sepharose followed by anion exchange chromatography on TMAE-Fractogel (EM Merck). Purification of fusion protein C was the same as for antibody A except that the protein was further purified by a hydrophobic interaction chromatography on a phenyl-Sepharose column (Amersham Biosciences) before the size exclusion chromatography.

Antibody A Binding Assay—The ability of monoclonal antibody A and its mutants to bind to antigen protein was tested in an ELISA assay. Individual wells in a 96-well plate were coated overnight using the antigen protein at 2 g/ml. Antibody A and its mutants were titrated into the plate at concentrations from 5 g/ml to 24 pg/ml and then incubated for 1 h. Binding of antibody A or its mutant to the antigen protein was detected by subsequent binding of horseradish peroxidase anti-human IgG and reaction with tetramethylbenzidine.

Deglycosylation of Proteins—N-Linked glycans were removed from the proteins with peptideN-glycosidase F. About 1 l of peptide N-glycosidase F (2.5 milliunits/1, Prozyme) was added to 25 l of a solution containing about 40 g protein, after which the solution was incubated at 37° C. overnight. Intact Mass Measurement—N-Deglycosylated proteins were reduced with 40 mM dithiothreitol in phosphate-buffered saline, pH 7.6, containing 4 M urea. The samples were then analyzed on an LC-MS system composed of an HPLC solvent delivery system (2695 Alliance Separations Module), a 2487 dual wavelength UV detector, and an LCT mass spectrometer (Waters Corp.). A Vydac C4 cartridge was used for desalting. Molecular masses were obtained by deconvolution of raw mass spectra using the MaxEnt 1 program embedded in MaxLynx 4.0 software (Waters Corp.).

Endo-Lys-C Peptide Mapping—Proteins were reduced and alkylated essentially as described in Wen et al. (18). The reduced and alkylated protein was digested with 10% (w/w) of endo-Lys-C (Roche) in 2 Murea, 0.12 MTris-HCl, pH 8.0, for 8 h at room temperature. Portions of this solution were analyzed on an LC-MS system described above. Peptides from the digest were eluted from a 1.0-mm 25-cm YMC C18 column (Waters Corp.) with a 185-min water, acetonitrile gradient (0-70% acetonitrile) containing 0.03% trifluoroacetic acid at a flow rate of 0.07 ml/min at 30° C.

Identification of Peptides by Mass Spectrometry—Peak components on the peptide maps were identified using MassLynx 4.0 software (Waters Corp.). MS/MS spectra were acquired using information-dependent acquisition on a nanoflow LCMS/MS system composed of a nano-flow HPLC (Dionex, Sunnyvale, Calif.) and a QSTAR XL mass spectrometer (Applied Biosystems, Foster City Calif.). The HPLC was equipped with a 0.3-mm 1-mm Pepmap C18-trap column for desalting and a 0.075-mm 150-mm, 100-Å, Pepmap C18 column for separation. Peptides were eluted with a 70-min linear gradient (0-50% acetonitrile) containing 0.1% formic acid at a flow rate of 0.2 l/min. The nanoelectrospray was generated with a nanoelectrospray ionization source (Sciex) using a Picoview needle (15-m inner diameter; New Objectives) maintained at a voltage of 1700 V. MS/MS spectra were in the m/z range 50-2000, and the collision energy setting was optimized for broader sequence coverage.

Spiking Experiments—Both the wild type and mutant protein samples were diluted to 0.50 mg/ml with phosphate-buffered saline. The concentration of the protein was calculated from its UV absorbance at 280 nm using a calculated extinction coefficient (A280 (1 mg/ml) 1.4 ml/mg m). To determine the detection limit of the Asn→Ser substitution, different amounts (0.025-25%) of a monoclonal antibody (mAb) with Asn3Ser mutations at residue 163 in the light chain and residue 392 in the heavy chain were spiked into the wild type mAb, using lowest-volume microsyringes. For analysis by intact mass measurement, an aliquot containing 100 pmol of the protein was injected; for analysis by peptide mapping, 250 pmol was injected. The samples were analyzed in triplicate in each case; the sample with the lowest concentration of Asn→Ser mutant spike was run first followed by increasingly higher concentrations of spike. Between sample runs, the column was cleaned by injecting water and running the gradient. For intact mass measurement data, the amount of the Asn→Ser substitution was calculated by comparison of the heights of peaks of MH10 10, MH15 15, and MH16 16 ions from the light chain. For peptide mapping data, the amount of the substitution was estimated from peak heights of the combined mass spectra for the predicted peptide and for the corresponding Asn→Ser-containing peptide, after subtracting background noise.

Results

Discovery of Low Mass (27 Da) Components—Antibody A is a humanized monoclonal antibody raised against a human protein. To ensure that a cell line selected for production of clinical study materials does not produce a protein with unexpected mutations or modifications, we analyzed samples of antibody A made from candidate cell lines using mass spectrometry. Unexpectedly, in addition to the expected light chain mass (observed 23,909 Da; calculated 23,910.8 Da) and heavy chain mass (observed 49,756 Da; calculated 49,757.2 Da), two minor components with masses of 23,882 and 49,728 Da were detected in the respective chains of some of the candidate cell line samples. The masses of these species were about 27 Da lower than those calculated for the light chain and the heavy chain, respectively. The amount of the "27 Da" component in each candidate cell line sample varied. FIGS. 1, C and D, shows the mass spectra of candidate cell line CL 24-34 as an example of one of the worst cases. The 27-Da components were absent when the antibody was produced in a low-expressing cell line (mAb A-1) as shown in FIGS. 1, A and B.

Figure 2:
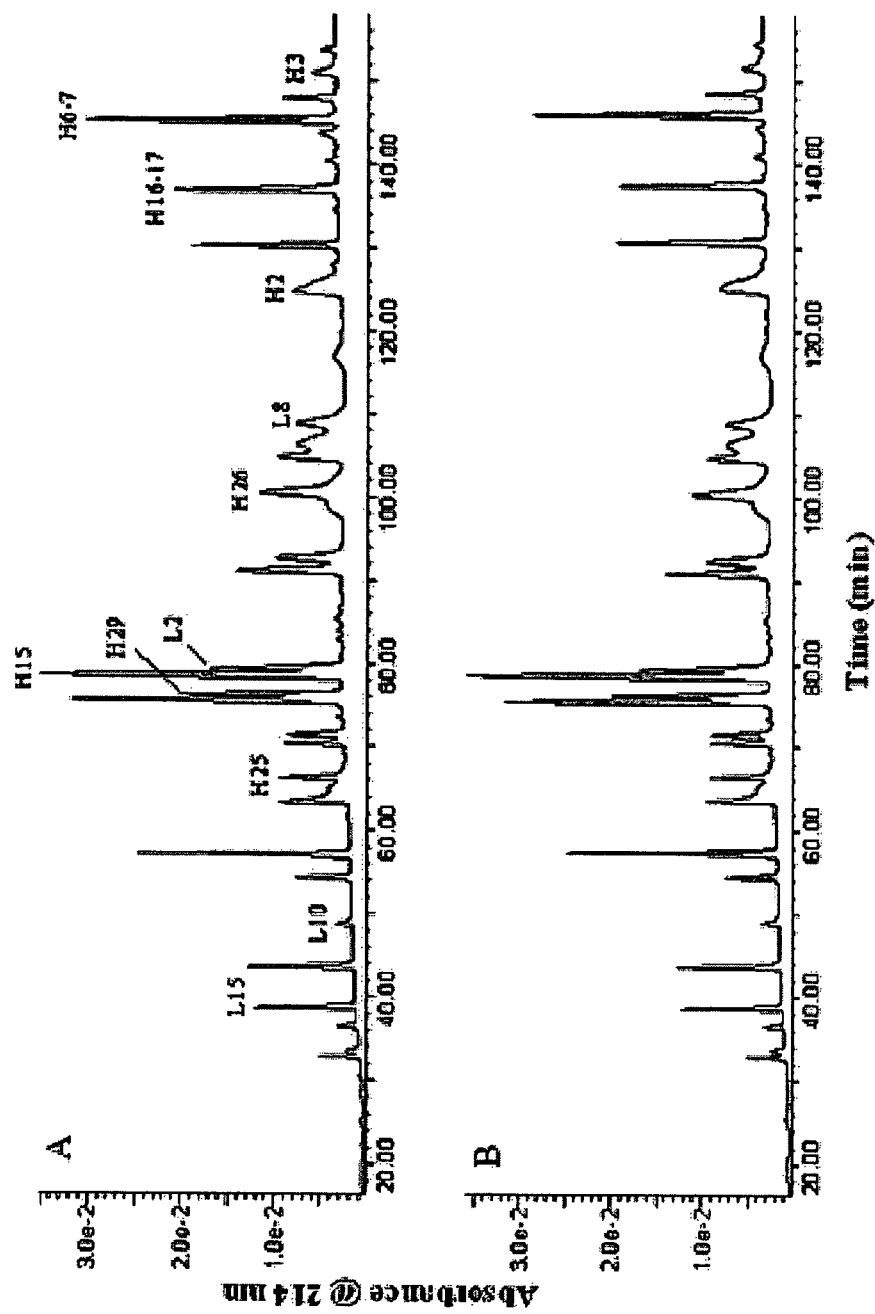
FIG. 2. UV profile with monitoring at 214 nm for endo-Lys-C peptide maps of the reduced antibody A. A, shown is mAb A-1. B, shown is a batch from candidate cell line CL24-34.
Figure 3:
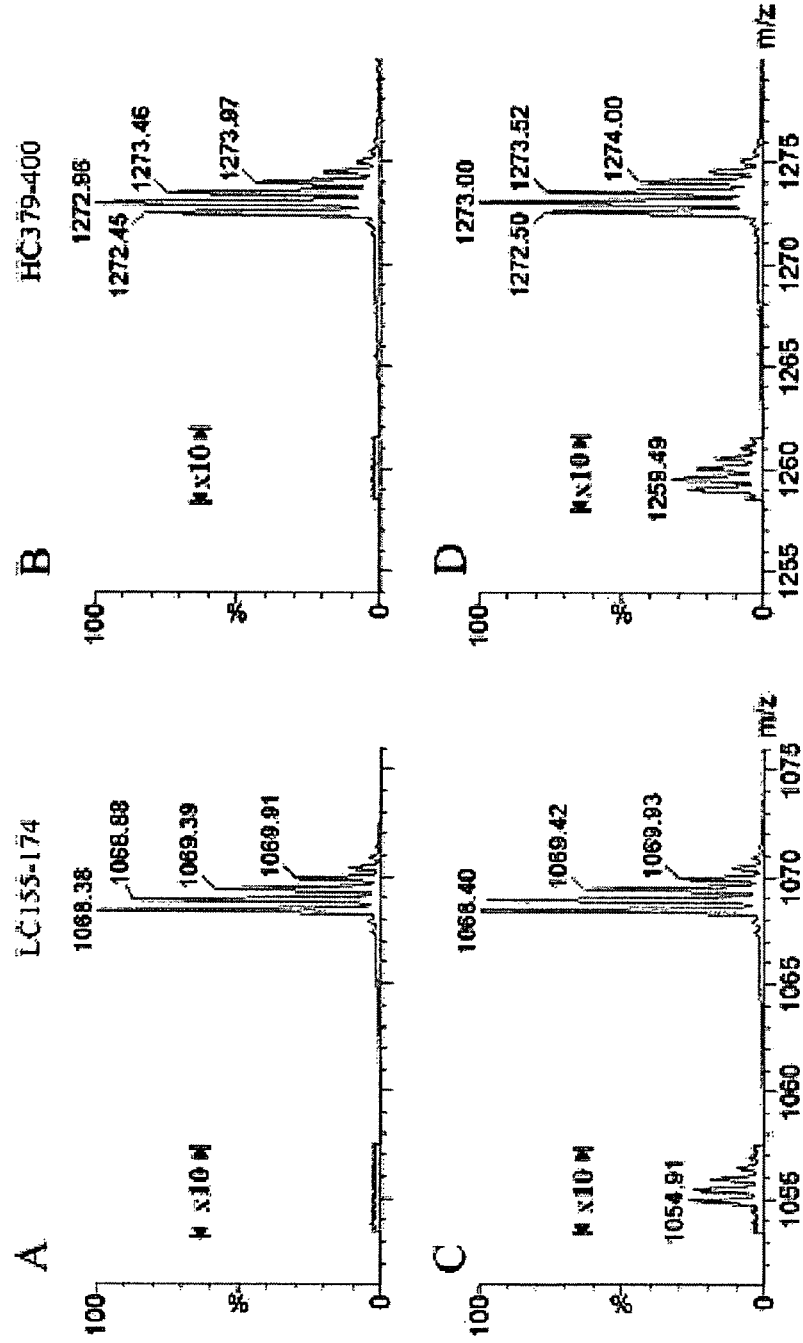
FIG. 3. Mass spectra of peptide LC 155-174 (A and C) and HC 379-400 (B and D) of antibody A. Only peaks in the doubly charged state are shown. A and B, shown are mAb A-1. C and D, shown is a batch from candidate cell line CL 24-34. The intensities of peaks near m/z 1055 and 1260 were increased 10-fold for easy viewing and comparison.
Figure 4:
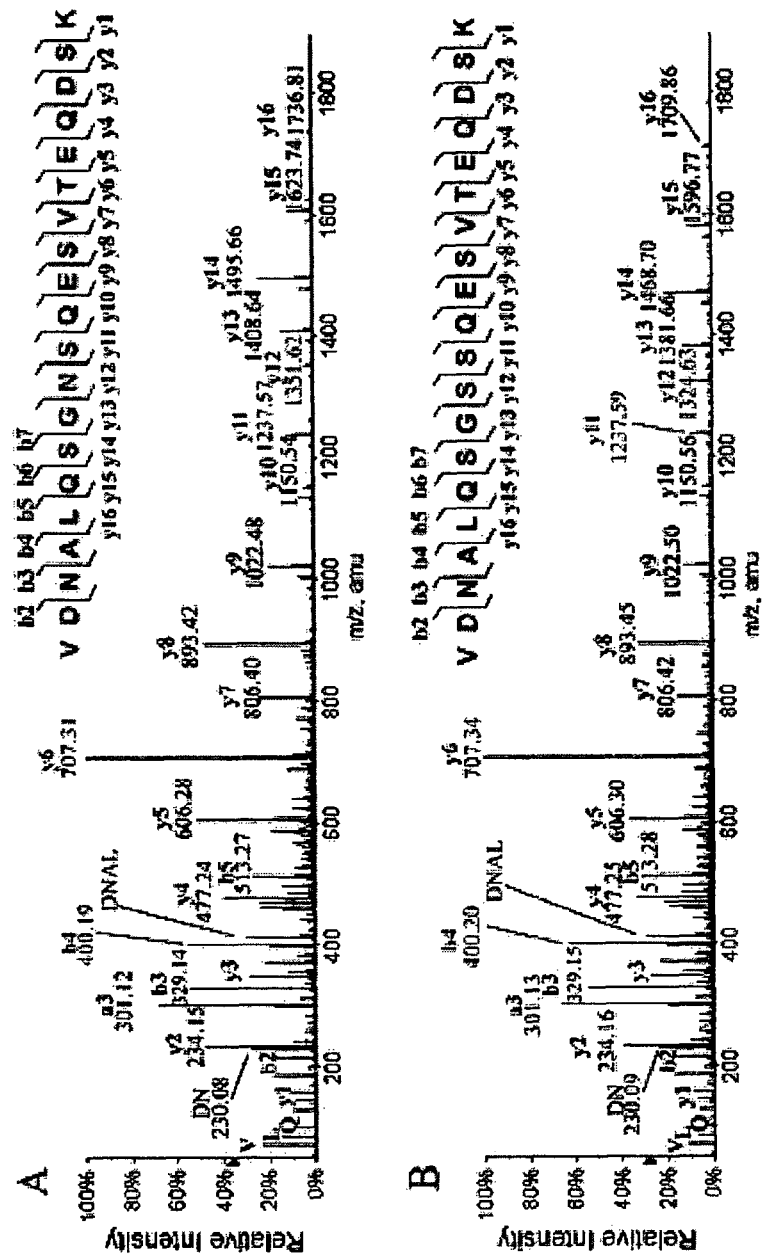
FIG. 4. MS/MS spectra of peptide LC 155-174 of antibody A. A, shown is the wild type peptide. B, shown is the peptide with an Asn→Ser substitution. The sequence of the peptide, the fragmentation pattern, and the detected fragment ions are shown at the top of each panel. Y ions contain the C-terminal region of the peptide, and b ions contain the N-terminal regions of the peptide. Calculated m/z values are y11=1237.55 and y12=1351.60 when residue 163 is Asn, and y11=1237.55 and y12=1324.59 when residue 163 is Ser.
Figure 5:
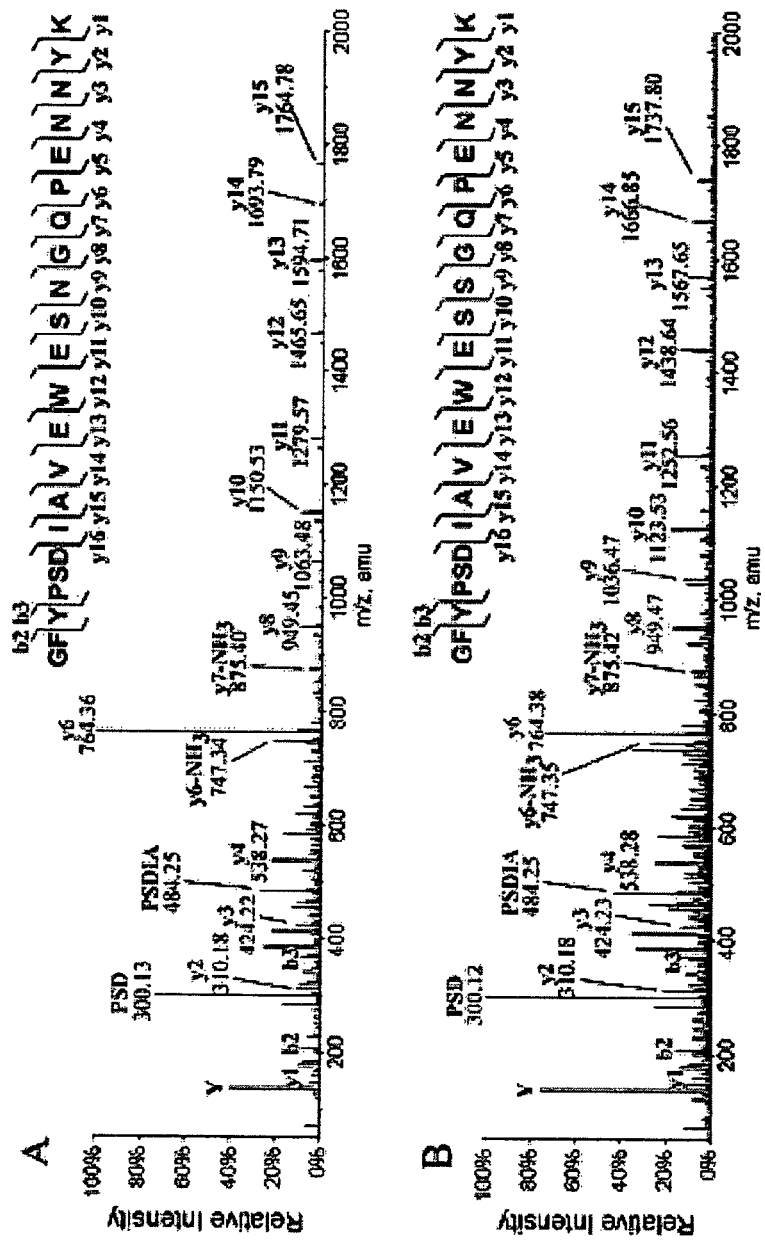
FIG. 5. MS/MS spectra of peptide 379-400 of antibody A. A, shown is the wild type peptide. B, shown is the peptide with an Asn-Ser substitution. The sequence of the peptide, the fragmentation pattern, and the detected fragment ions are shown at the top of each panel. Y ions contain the C-terminal region of the peptide, and b ions contain the N-terminal regions of the peptide. Calculated m/z values are y8=949.44 and y9=1063.48 when residue 387 is Asn, and y8=949.44 and y9=1036.47 when residue 387 is Ser.

Identity of the Low Mass (27 Da) Components—To identify the 27-Da species seen for both the light chain and the heavy chain of the antibody, we carried out endo-Lys-C and endo-Asp-N peptide mapping of the reduced antibody A using an LC-MS system. The sequence coverage of the combined endo-Lys-C and endo-Asp-N peptide maps for antibody A is 100% for both the light and heavy chains (data for the endo-Asp-N peptide maps are not shown). FIG. 2 shows the HPLC profile, monitored at 214 nm, for endo-Lys-C peptide digests of samples of the mAb A-1 and of cell line candidate CL 24-34. Comparison of the UV profiles and total ion chromatograms for the two samples did not reveal any obvious differences between samples. However, when we carefully compared the mass spectral profiles peak by peak, we observed low levels of extra components in the map of the CL 24-34 sample, specifically components whose molecular masses were all 27 Da lower than the nearby peptides having the expected masses. For example, FIG. 3 shows mass spectra of a light chain peptide, LC 155-174, and of a heavy chain peptide, HC 379-400, from samples CL 24-34 and mAb A-1. There are four possible changes that could produce a peptide with a molecular mass of 27 Da lower than predicted: Arg3Glu, Gln3Thr, Lys3Thr, or Asn3Ser. We found that the 27-Da components were detected only when the corresponding normal peptides contained an Asn residue (see FIG. 2 and Table 1) and, therefore, concluded that the 27-Da components detected in candidate cell line samples must be due to an Asn→Ser substitution. To confirm this, several of the 27-Da-containing peptides were subjected to MS/MS sequencing analysis along with their "normal" corresponding peptides as controls. During MS/MS sequencing analysis, the peptide is fragmented by collision-induced dissociation, which breaks backbone amide bonds generating a series of fragment ions, mainly C-terminal y ions and N-terminal b ions in this case. The identity of an amino acid at each position in a peptide can be determined by the difference in the m/z values of two adjacent y or b ions. For example, a difference of 114 atomic mass units between adjacent y ions (or b ions) indicates an Asn at that position, and a difference of 87 atomic mass units indicates a Ser. FIG. 4A shows the MS/MS spectrum of the predicted peptide LC 155-174 (i.e. a light chain peptide containing predicted residues 155-174). There are two Asn residues in peptide LC 155-174, at positions 157 and 163, based on the predicted sequence. As shown in FIG. 4A, the differences in m/z values between y12 (1351.62) and y11 (1237.57) and between b3 (329.14) and b2 (230.08) are each 114.04, confirming Asn at the both positions in this peptide as predicted. LC-MS peptide mapping detected two 27-Da components related to peptide LC 155-174; one co-eluted with the predicted wild type peptide, and the other eluted slightly later. FIG. 4B shows a MS/MS spectrum for the 27-Da component that eluted slightly later. As one can see in this spectrum, the difference of m/z values between b3 (329.15) and b2 (230.09) is 114.04, confirming an Asn at position 157. However, the difference of m/z values between y12 (1324.63) and y11 (1237.59) is 87.03, indicating that a Ser is at the position 163, not the predicted Asn. The differences in m/z values for the other adjacent ions in this peptide are all as expected, which confirms that the sequence of the rest of the peptide is the same as the wild type. The MS/MS sequencing analysis of the 27-Da component that co-eluted with the wild type peptide showed that a Ser replaced Asn-157 in the peptide but not Asn-163 (data not shown). Similarly, there are three 27-Da components related to peptideHC379-400 (residues 379-400 in the heavy chain). FIG. 5 shows the MS/MS spectrum of one of three peptides along with the corresponding wild type peptide HC 379-400; Asn is at position 392 in the wild type peptide as predicted (FIG. 5A; the difference in m/z values for y9 (1063.48) and y8 (949.45) is 114.04), but Ser is at this position in the 27-Da-containing peptide (FIG. 5B; the difference in m/z values for y9 (1036.47) and y8 (949.47) is 87.03). MS/MS sequencing of the other two 27-Da-containing peptides demonstrated that the 27-Da peptide was also because of an Asn3 Ser substitution (data not shown) antibody A contains 7 Asn residues in the light chain and 18 in the heavy chain. A combination of endo-Lys-C and endo-Asp-N peptide mapping detected Asn→Ser substitutions at all the predicted Asn positions, including the predicted N-glycosylation site Asn-305 in the Fc region. Table 1 summarizes the results. The Asn→Ser substitution occurred randomly in the antibody polypeptide chains, with about 1-2% at each Asn position in the CL 24-34 sample; no preferred site was observed. In addition, we detected by peptide mapping Asn→Ser substitution in the samples made in many candidate cell lines, the level varying from 0.3 to 2% per Asn position.

TABLE 1

Predicted endo-Lys-C peptides for antibody A (huP2D10v2) and summary results of Asn →Ser substitution analysis

| Endo-LysC peptide (residues) | Number of Asn residues in the peptide | Amount of Asn → Ser[a] % |
|---|---|---|
| Antibody A, light chain | | |
| L1 (1-33) | 0 | |
| L2 (34-44) | 1 (CDR1) | 1.4 |
| L3 (45-55) | 0 | |
| L4 (56-79) | 1 (CDR2) | 1.5 |
| L5, L6, L7, L6 (80-131) | 0 | |
| L8 (132-150) | 2 | 3.0 |
| L9 (151-154) | 0 | |
| L10 (155-174) | 2 | 3.1 |
| L11, L12, L13, L14 (175-212) | 0 | |
| L15 (213-219) | 1 | 1.6 |
| Antibody A, heavy chain | | |
| H1, 1-43 | 0 | |
| H2, 44-76 | 1 | 1.9 |
| H3, 77-129 | 2 | 4.0[b] |
| H4, H5 (130-155) | 0 | |
| H6-7, 156-218 | 4 | 6.7 |
| H8, H9, H10, H11 (219-230) | 0 | |
| H12, H13, H14 (231-282) | 0 | |
| H15, 283-296 | 2 | 2.4[b] |
| H16-17, 297-325 | 2 | 2.9 |
| H18, H19 (326-330) | 0 | |
| H20, 331-334 | 1 | 1.4[b] |
| H21, H22, H23, H24 (335-368) | 0 | |
| H25, 369-378 | 1 | 1.4 |
| H26, 379-400 | 3 | 4.6 |
| H27, H28 (401-422) | 0 | |
| H29, 423-447 | 2 | 2.8 |
| H30, 448-454 | 0 | |

[a]The amount of the substitution was estimated from peak heights of the combined mass spectra from the extracted ion chromatograms of the predicted peptide and the corresponding peptide containing the Asn → Ser substitution.
[b]Amounts are estimated from the endo-Asp-N peptide map of the protein (data are not shown).

Figure 6:
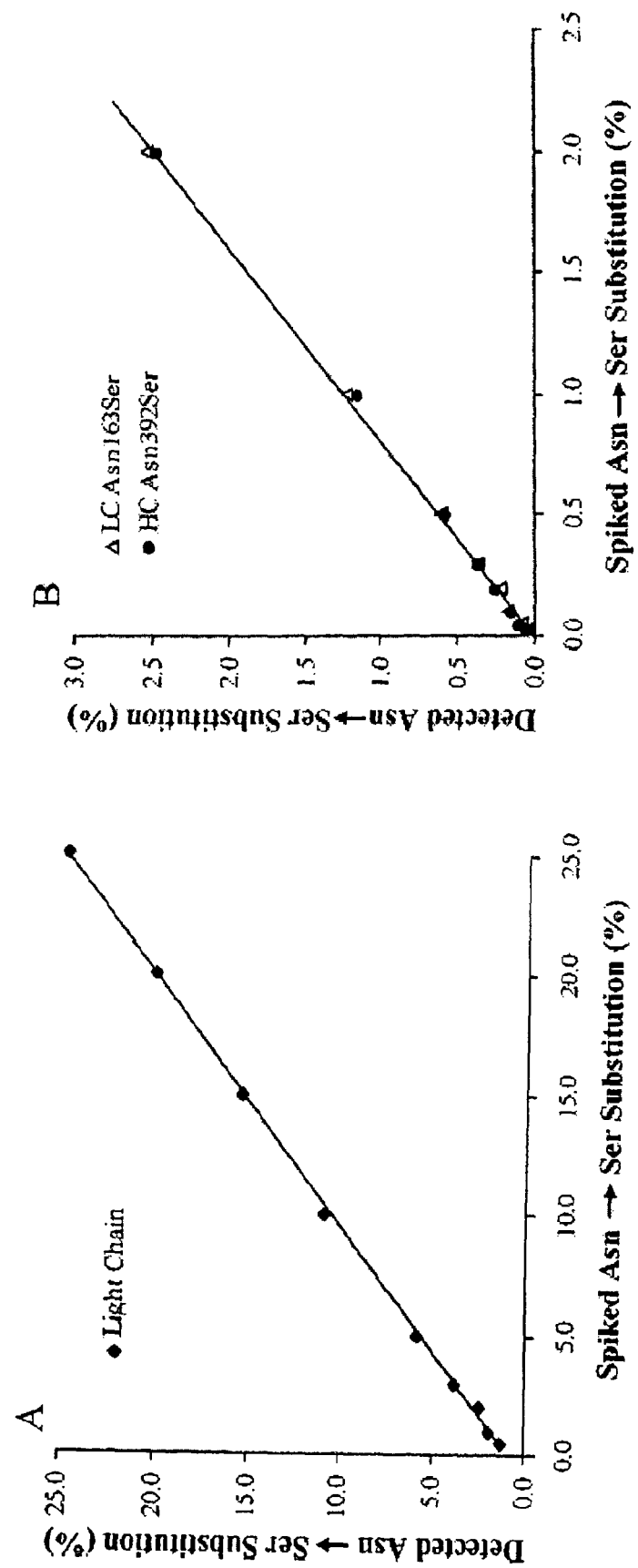
FIG. 6. Plots of the detected amounts of the Asn→Ser substitution in monoclonal antibody samples that were spiked with varying amounts of a monoclonal antibody with Asn→Ser mutations at residue 163 in the light chain and at residue 392 in the heavy chain. A, shown is intact mass measurement for the light chain of antibody A. B, shown is peptide mapping of antibody A. LC, light chain; HC, heavy chain.

Limits of Detection of Asn→Ser Substitutions Using Intact Mass Measurement and Peptide Mapping—To determine the limits of detection for the intact mass measurement and peptide mapping methods, spiking experiments were carried out using a mutant of antibody A, L163/H392, in which residue Asn-163 in the light chain and residue Asn-392 in the heavy chain had been mutated to Ser. The wild type protein (mAb A-1) was then spiked with the mutant, and the lowest levels of detection were determined. These experiments showed that 0.5% of an Asn3Ser substitution in the light chain (FIG. 6A) or 2% in the heavy chain (data not shown) of antibody A could be detected by intact mass measurement using 100 pmol of the reduced protein, and that using endo-Lys-C peptide mapping and 250 pmol of the reduced protein, 0.025% of an Asn3Ser substitution in a peptide could be detected. The mass spectrometric response to substitution in a peptide is linear and the intercept is very close to zero (FIG. 6B). However, the observed amounts of the mutant peptides on a particular peptide map are about 15-20% higher than spiked values, which is partly caused by better ionization (12% better, data not shown) of the Ser mutant peptide compared with its wild type form and partly caused by partial saturation of the wild type peptide in the electrospray ionization-time of flight mass spectrometer used in this study. This work also showed that 2% of the mutant is required for quantification of the Asn3Ser substitution in the intact light chain or 0.1% in a peptide. The degree of substitution from intact mass measurement for the heavy chain cannot be used for estimating the overall amount of substitution because the mutant and wild type forms of the heavy chain are poorly resolved.

Investigation of the Cause of the Asn3Ser Substitution—As mentioned above, the Asn3Ser substitution was observed in samples made from all candidate cell lines that had been produced by independent transfections (rows 3, 4, and 6 in Table 2). Furthermore, substitution was detected at all Asn positions in the protein and at similar levels (Table 1). It, therefore, seemed that the substitution was not due to a particular cell line. To confirm this and to find out whether the Asn→Ser substitution was due to variations in cell culture conditions in the shake flasks, where pH, oxygen sparge rate, etc., were not tightly controlled, we expressed antibody A from different cell lines in bioreactors before and after amplification. As shown in Table 2, the Asn3Ser substitution was also observed in samples made in bioreactors regardless of which cell line was used (rows 5, 7, 10, and 13) whether or not amplification was done (rows 5 versus 8) and whether the cells were harvested at days 7 or 14 (rows 9 versus 10 and rows 11 versus 12). Although we found that the amount of the substitution varies between cell lines, no trend was found; the protein made from cell line CL 24-34 (row 4) had the highest level of substitution of all the samples made in shake flasks, but the protein made from the same cell line in a bioreactor had a very low level of the substitution (row 13). On the other hand, the samples from cell line CL 24-13 had similar amounts of the substitution regardless of whether they were made in a shake flask or a bioreactor (rows 3 and 8). Furthermore, the level of the substitution in one sample harvested at day 7 was lower than that from day 14 (row 9 versus 10) but higher at day 7 compared at day 14 in another sample (rows 11 versus 12). Therefore, we concluded that the Asn→Ser substitution is not due to the cell lines used. Because we had not observed the Asn→Ser substitution in any recombinant proteins made previously and had not seen any reports of this problem in the literature, we thought that the Asn→Ser substitution might be antibody A molecule-specific. To test the idea, we made two other proteins under the same culture conditions; antibody B (raised against a very different target antigen) and fusion protein C. Once again endo-Lys-C peptide mapping of the two samples revealed the Asn→Ser substitution in many Asn-containing peptides for both proteins. The substitution level was about 0.4% at each Asn position for antibody B and about 0.2% for fusion protein C (supplemental Table 1 and supplemental FIGS. 1 and 2). Thus, the Asn3Ser substitution is not protein molecule-specific. These results suggested that cell culture conditions might be responsible for the Asn3Ser substitution. We tested various culture conditions using different in-house-made media (M1, M2, and M3) and feeds (F1, F2, F3, F4, and F5 with or without hydrolysates and Asn). Representative results are shown in Table 2. Our experiments showed that the substitution could occur in proteins made in medium M1, M2, or M3 that contain 0.2-0.9 g/liter L-Asn monohydrate. The Asn→Ser substitution was not detected in the mAb A-1 but was observed in protein made from a high-expressing cell line grown in the same medium (M1) with the same feed (F1), which contains 2.4 g/liter L-Asn (rows 1 versus 2). Although it seemed that the Asn→Ser substitution was related to the higher product titer in the cell culture, our studies did not show a linear relationship between the level of the Asn3Ser substitution and the product titers in bioreactors, at least not within our testing range (1-4.2 g/liter, rows 7, 8, 10, 12-14 in Table 2). When M1 and M2 media were tested using different feeds, the substitution was not observed when the culture was augmented with Asn at a high concentration, i.e. in culture with optimized feed containing additional L-Asn (F5 contains 4.5 g/liter Asn, rows 15 and 16 in Table 2), or when L-Asn was added to an optimized feed (row 18 in Table 2). Further experiments showed that the results were reproducible and that the strategy of adding L-Asn in the feed could be scaled up for a 200-liter bioreactor. Thus, we demonstrated that Asn3Ser substitution was caused by starvation for L-Asn in the cell culture medium.

TABLE 2

Summary results of Investigations Into the causes of the Asn →Ser substitution

| | | Sample information | | | | | | Estimated degree |
|---|---|---|---|---|---|---|---|---|
| Row no. | Cell line | SF/BR[a] | Temperature °C. | Medium | Feed[b] | Day | Titer[c] mg/liter | of Asn → Ser substitution |
| 1 | mAb A-1 | BR | 37/28 | M1 | F1 | 14 | 80 | Not detected |
| 2 | CL 24-13 | SF | 37/28 | M1 | F1 | 16 | 566 | 2 |
| 3 | CL 24-13 | SF | 36 | M2 | F2 + hydrolysates | 16 | 821 | 6 |
| 4 | CL 24-34 | SF | 36 | M2 | F2 + hydrolysates | 16 | 689 | 7 |
| 5 | CL 24-13 | BR | 35 | M1 | F4 + hydrolysates | 14 | 2582 | 6 |
| 6 | CL 29-13 | SF | 35 | M2 | F4 | 14 | 546 | 2 |
| 7 | CL 29-13 | BR | 35 | M2 | F4 + hydrolysates | 14 | 1032 | 10 |
| 8 | CL 13-21 (progeny CL 24-13) | BR | 35 | M2 | F4 + hydrolysates | 12 | 2887 | 8 |
| 9 | CL 9-05 (progeny CL 17-14) | BR | 36.5 | M2 | F4 + hydrolysates | 7 | 500 | 2 |
| 10 | CL 9-05 (progeny CL 17-14) | BR | 36.5 | M2 | F4 + hydrolysates | 14 | 2057 | 4 |
| 11 | CL 13-01 (progeny CL 24-13) | BR | 36.5 | M2 | F4 + hydrolysates | 7 | 600 | 8 |

TABLE 2-continued

Summary results of Investigations Into the causes of the Asn →Ser substitution

| Row no. | Cell line | Sample information | | | | | Titer[c] mg/liter | Estimated degree of Asn → Ser substitution |
| | | SF/BR[a] | Temperature ° C. | Medium | Feed[b] | Day | | |
|---|---|---|---|---|---|---|---|---|
| 12 | CL 13-01 (progeny CL 24-13) | BR | 36.5 | M2 | F4 + hydrolysates | 14 | 1377 | 6 |
| 13 | CL 15-29 (progeny CL 24-34) | BR | 36.5 | M2 | F4 + hydrolysates | 14 | 4162 | 2 |
| 14 | CL 13-21 (progeny CL 24-13) | BR | 35 | M2 | F4 | 14 | 2497 | 5 |
| 15 | CL 13-21 (progeny CL 24-13) | BR | 35 | M3 | F5 + hydrolysates | 14 | 1128 | Not detected |
| 16 | CL 15-29 (progeny CL 24-34) | BR | 35 | M3 | F5 + hydrolysates | 14 | 1312 | Not detected |
| 17 | CL 13-21 (progeny CL 24-13) | BR | 35 | M2 | F4 + hydrolysates | 14 | 3274 | 4 |
| 18 | CL 13-21 (progeny CL 24-13) | BR | 35 | M2 | F4 + hydrolysates + Asn | 14 | 2991 | Not detected |
| 19 | Antibody B | BR | 35 | M2 | F4 + hydrolysates | 14 | 2073 | 3 |
| 20 | Fusion Protein C | BR | 35 | M3 | F3 | 14 | 894 | 2 |

[a]BR = bioreactor; SF = shake flask.
[b]F1, F2, F3, F4, and F5 contain 2.4, 1.5, 0.0, 1.5, and 4.5 g/liter of Asn•$H_2O$, respectively.
[c]Titer of the expressed protein.

Binding of an Asn3Ser Mutant of Antibody A—Antibody A has two Asn residues in the complementarity determining region of the light chain. To test whether the Asn→Ser substitution would affect the function of the antibody, an antibody A mutant was made in which Asn-35 in the light chain was mutated to Ser (LC-N35S). The binding affinity of the LC-N35S to the antigen protein was tested and compared with the wild type antibody A. As shown in supplemental FIG. 3, no significant difference was detected in the binding affinity between the LC-N35S mutant and wild type antibody A.

Discussion

We have discovered that Ser can be misincorporated randomly at Asn positions when proteins are expressed at very high levels in CHO cells. Using our methods, 1% of an Asn3 Ser substitution in a 20-kDa protein can be detected by mass measurement of the intact protein, and 0.03% of the substitution can be detected in a peptide, e.g. by peptide mapping analyses. Further investigation showed that the substitution was due to starvation for Asn and that adding extra Asn to culture medium can overcome the problem. Random amino acid substitutions in proteins occur naturally. The frequency of the errors under subnormal growth conditions occurs at a rate of about 4 10 4 to 5 10 5 per codon, or 0.005-0.04% per site (12). However, the error frequency can be 20-150-fold higher under conditions of stress (10). The fidelity of protein biosynthesis depends on accurate codon-anticodon interaction between mRNA and tRNA and also on the specific attachment of amino acids to their cognate tRNA species. Random amino acid substitution can be caused by either an anticodon-codon mismatch, i.e. misreading, or the use of an erroneously charged tRNA, i.e. mischarging or misacylation (12).

We believe that the misincorporation of Ser at Asn positions was due to mischarging of tRNAAsn rather than misreading for three reasons. First of all, it has been shown that most misreading errors occur at the third position of the codon, which has a weaker interaction with its cognate base than do bases at the first and second positions (20, 21). So far, all Asn starvation experiments have shown that the Asn codons AAU and AAC were misread as lysine, AAA and AAG, errors at the third position of the codon (22, 23). Second, Asn starvation studies have also shown (24, 25) that the frequency of misreading of the Asn codon, AAU, is much higher (2-10-fold) than for the AAC codon, whereas we see no codon preference even though about two-thirds of the Asn codons in our proteins are AAU. Third, mischarging, as seen here, is not codon-related but results from the attachment of a different but structurally related amino acid to its cognate tRNA; misincorporation can be prevented by supplementing the culture medium with the cognate amino acid, Asn, in this case (11, 26). Acylation of tRNA is a two-step reaction: the amino acid is activated by ATP to form an aminoacyl-adenylate intermediate (aa-AMP), and then the intermediate reacts with the tRNA to produce aminoacyl-tRNA and AMP. Acylation of tRNAs is controlled by aminoacyl-tRNA synthetases (aminoacyl-RSs) which not only catalyze the reactions but also employ proofreading or editing mechanisms at various steps during the catalytic cycle to ensure that cognate amino acids are attached to the appropriate tRNAs. Complete discrimination of amino acids by aminoacyl-RSs is achieved through different strategies. First of all, aminoacyl-RSs have to recognize their cognate amino acids in intracellular pools of amino acids. About half of the aminoacyl-RSs can easily recognize their cognate amino acids based on structural or chemical and physical properties, such as size, charge, hydrophobicity, and space orientation as these enzymes produce conjugates with molecular geometries for cognate amino acids and unfavorable geometries for noncognate amino acids. However, in the case of substrates with close structural and chemical similarities, the enzymes use proofreading or editing strategies during the process of tRNA aminoacylation to ensure high accuracy of protein biosynthesis. Fidelity mechanisms of the aminoacyl-RSs with known editing functions have been reviewed thoroughly recently by Mascarenhas et al. (27) and Splan et al. (28). To ensure fidelity, misactivated aminoacyl-adenylates and misaminoacylated tRNAs can be hydrolyzed in respective pre-transfer editing and post-transfer editing processes. Some non-cognate amino acids are edited at the synthetic active site, and others are edited at a separate editing site in the aminoacyl-RS. Hydrolysis of misacylated tRNA can occur in a distal hydrolytic active site or in an editing domain in an aminoacyl-RS (29-32). The mechanism for hydrolysis of non-cognate aminoacyl-adenylates is not completely understood yet, but several mechanisms have been proposed including hydrolysis in a distinct editing active site after translocation to it (33, 34), hydrolysis within the synthetic active site (35, 36), and selective release into the cellular milieu (36, 37). Recent studies have shown that editing-like reactions can occur within the synthetic active site in glutaminyl-RS (a class I aminoacyl-RS) (35), prolyl-RS (a class II aminoacyl-RS) (37), and seryl-RS (a class II aminoacyl-RS) (38). Asparaginyl-RS, a class IIb aminoacyl-RS, does not possess an editing domain (39), and so far no editing activity for asparaginyl-RS has been reported, which suggests that asparaginyl-RS can select its cognate substrates from a pool of competitive substrates in a very efficient initial binding step based on structure and physical and chemical properties. It is probably true that when Asn is in good supply for protein biosynthesis, asparaginyl-RS has the highest binding affinity for Asn and the lowest hydrolysis rate for asparaginyl-adenylate compared with non-cognate aminoacyl-adenylates. However, when Asn is not present in sufficient amounts, other amino acids, especially ones with the most similar structures and physical and chemical properties, will be misactivated so that biosynthesis can continue. The misincorporation of norvaline, a non-protein amino acid, at leucine positions in recombinant human hemoglobin when the ratio of norvaline to leucine in culture medium is high is a good example (11). Why is it that Ser rather than other amino acids is misincorporated at Asn positions? Both Asn and Ser are neutral, polar amino acids, with similar physical properties. Although aspartic acid is the closest structural analog for Asn, it does not bind to the synthetic active site in asparaginyl-RS because Glu-225 in asparaginyl-RS has a dual role of positive recognition of Asn and discrimination against the negatively charged aspartic acid side chain (39). Calculated binding energies also suggest that Ser will compete with Asn for formation of an activated intermediate with asparaginyl-RS (40). In addition, both asparaginyl-RS and seryl-RS are class II aminoacyl-RSs that share many structural features. For example, both are homodimers and lack an editing domain, and their size and catalytic domains are similar (41, 42). The structure of the asparaginyl-tRNA synthetase-ATP complex has exactly the same configuration of three divalent cations as does the seryl-RS-ATP complex (39), indicating that the structure of Ser is similar to that of Asn. Overall, the slightly smaller size of Ser and similar physical and chemical natures of Ser and Asn seem to result in a higher binding affinity of Ser at the synthetic active site and slower rate of hydrolysis of seryl-AMP in asparaginyl-RS than for other amino acids assuming that the same pre-transfer editing exists in asparaginyl-tRNA synthase as in seryl-RS (38). Thus, tRNAAsn appears to have been misacylated by Ser but not other amino acids when there is a shortage of Asn during protein biosynthesis. Based on our results we propose a model for Ser misincorporation at Asn positions. Asparagine is a nonessential amino acid that can be supplied by biosynthesis in CHO cells under normal biosynthesis conditions. Whenever CHO cells need Asn, the extent of aminoacylation of tRNAAsn decreases, and the activity of Asn synthetase for production of Asn amino acid increases 43, 44). Thus, cells regulate themselves to meet their requirement for Asn. Asparaginyl-RS has the highest selectivity for Asn and does not need significant editing activities as do other aminoacyl-RSs. Asparaginyl-RS excludes non-cognate amino acids that are larger than Asn, e.g. Gln, Glu, Ile, Leu, Val, Met, etc. It does not bind smaller amino acids (Ala, Pro, and Gly) whose side chains cannot form hydrogen bonds with residues in its synthetic active site (39), it does not bind Asp because Glu-225 in the synthetic active site repels the negatively charged side chain of Asp (39), it cannot bind Cys tightly because it cannot provide the zinc-thiolate interaction required for binding Cys to cysteinyl-RS (45), and it does not bind well with Thr because the methyl group of the side chain of Thr is bulky and hydrophobic and because the geometry of the side chain is very different from Asn. Ser is the only amino acid that is both smaller than Asn and has some similar hydrogen-bonding properties. Thus, Ser can bind to the active site in asparaginyl-RS relatively more tightly than can other non-cognate amino acids. However, the binding affinity of Ser to asparaginyl-RS will be much weaker than that of Asn as the hydroxyl group of its side chain can form only one hydrogen bond with a residue in the synthetic active site of asparaginyl-RS, whereas Asn can form two hydrogen bonds (with Glu-225 and Arg-368) (39). In addition, non-cognate-adenylates may be hydrolyzed at the synthetic active site of asparaginyl-RS, as has been reported for seryl-RS 38).

No miscorporation at Asn positions was observed when cells grew at a normal growth rate or when a sufficient amount of Asn was supplied in the culture medium. However, if the rate of Asn biosynthesis is not high enough to meet the need for overexpression of a foreign protein, the cells become starved for Asn, which can increase the rate of formation of misacylated adenylates and mischarged tRNAAsn. In this case the result is detectable Ser misincorporation at Asn positions in the protein, as Ser is the closest analog to Asn, and it is available. This problem can be corrected simply by adding adequate amounts of Asn to the cell culture medium. It is interesting that we did not detect any substitution of Asn by Lys, as noted by others (5, 22, 24) in *E. coli* under conditions of extreme Asn starvation. Perhaps it is because in all Asn starvation studies reported so far, the relevant asparaginyl-RS was inactivated by using temperature-sensitive asparaginyl-RS mutants. Thus, no tRNAAsn mischarging could have occurred, only misreading. Furthermore, Stanner et al. (47) have shown that asparaginyl-RS in CHO cells is much more sensitive to amino acid starvation than are other aminoacyl-RS s.

The large scale synthesis of recombinant proteins always involves overexpression of the product, which can lead to nutritional stresses in the production cells and create imbalances in the charged tRNA supply, resulting in a marked increase in the frequency of random translational errors. To date, most published data dealing with charged tRNA imbalances in overexpression systems used for making recombinant proteins refer to *E. coli*. Our finding of the Asn→Ser substitution is the first such report for proteins overexpressed in CHO cells under normal recombinant protein production conditions. This should not be a total surprise as the pathways of protein synthesis in prokaryotes and eukaryotes are similar, although the quality control for protein biosynthesis in eukaryotes is tighter than that in prokaryotes (17).

Although little is known about the possible deleterious effects in humans due to minor amounts of erroneously synthesized recombinant protein therapeutics, abnormal bioactivities and undesirable immune responses could be problems. For instance, diseases caused by editing-defective aminoacyl-RSs are well known (48-50); single Asn→Ser mutations have caused the loss in binding capacity in proteins (51-53), diminished enzymatic activity (54), and changed protein folding structure (55) and have been associated with diseases (46, 56, 57). We observed only a minor decrease of the binding affinity when Asn-35 was mutated to Ser in the complementarity determining region of the light chain of antibody A (supplemental FIG. 3), but the mutation could be immunogenic in vivo. Therefore, steps need to be taken both to identify and eliminate such potential errors when developing expression strategies for producing recombinant proteins used in human therapies, e.g. when limiting Asn in the culture media and feeds (19) to gain maximum growth rates and to reduce the amount of ammonia in CHO cell cultures. Random misincorporation is difficult to detect and quantify by conventional analytical methods, especially when the cognate and erroneous residues belong to similar chemical groups, as they manifest themselves as a heterogeneous mixture of proteins, each having slightly different chemical and physical properties from the other. Because removal of erroneously synthesized molecules after production is likely to be extremely difficult, it is better to prevent their formation in the first place, i.e. by careful monitoring for such errors when changing protein expression conditions using modern analytical tools as we have demonstrated here.

REFERENCES

1. Reichert, J. M., Rosensweig, C. J., Faden, L. B., and Dewitz, M. C. (2005) *Nat. Biotechnol.* 23, 1073-1078
2. Wurm, F. M. (2004) *Nat. Biotechnol.* 22, 1393-1398
3. Low, D., O'Leary, R., and Pujar, N. S. (2007) *J. Chromatogr. B Analyt. Technol. Biomed. Life Sci.* 848, 48-63
4. Birch, J. R., and Racher, A. J. (2006) *Adv. Drug Deliv. Rev.* 58, 671-685
5. Parker, J., Pollard, J. W., Friesen, J. D., and Stanners, C. P. (1978) *Proc. Natl. Acad. Sci. U.S.A.* 75, 1091-1095
6. Rosenberger, R. F. (1991) *Mutat. Res.* 256, 255-262
7. Scorer, C. A., Carrier, M. J., and Rosenberger, R. F. (1991) *Nucleic Acids Res.* 19, 3511-3516
8. Santos, M. A., and Tuite, M. F. (1993) *Trends Biotechnol.* 11, 500-505
9. Roserberg, R. F., and Holliday, R. (1993) *Trends Biotechnol.* 11, 498-499
10. Rosenberger, R. F. (1994) *Dev. Biol. Stand.* 83, 21-26
11. Apostol, I., Levine, J., Lippincott, J., Leach, J., Hess, E., Glascock, C. B., Weickert, M. J., and Blackmore, R. (1997) *J. Biol. Chem.* 272, 28980-28988
12. Parker, J. (1989) *Microbiol. Rev.* 53, 273-298
13. Spanjaard, R. A., Chen, K., Walker, J. R., and van Duin, J. (1990) *Nucleic Acids Res.* 18, 5031-5036
14. Brinkmann, U., Mattes, R. E., and Buckel, P. (1989) *Gene* 85, 109-114
15. Seetharam, R., Heeren, R. A., Wong, E. Y., Braford, S. R., Klein, B. K., Aykent, S., Kotts, C. E., Mathis, K. J., Bishop, B. F., Jennings, M. J., Smith, C. E., and Siegel, N. R. (1988) *Biochem. Biophys. Res. Commun.* 155, 518-523
16. Calderone, T. L., Stevens, R. D., and Oas, T. G. (1996) *J. Mol. Biol.* 262, 407-412
17. Ibba, M., and Soll, D. (1999) *Science* 286, 1893-1897
18. Wen, D., Wildes, C. P., Silvian, L., Walus, L., Mi, S., Lee, D. H., Meier, W., and Pepinsky, R. B. (2005) *Biochemistry* 44, 16491-16501
19. Seewoster, T., and Lehmann, J. (1995) *Appl. Microbiol. Biotechnol.* 44, 344-350
20. Lagerkvist, U. (1978) *Proc. Natl. Acad. Sci. U.S.A.* 75, 1759-1762
21. Lustig, F., Elias, P., Axberg, T., Samuelsson, T., Tittawella, I., and Lagerkvist, U. (1981) *J. Biol. Chem.* 256, 2635-2643
22. Parker, J., and Friesen, J. D. (1980) *Mol. Gen. Genet.* 177, 439-445
23. Parker, J., Johnston, T. C., Borgia, P. T., Holtz, G., Remaut, E., and Fiers, W. (1983) *J. Biol. Chem.* 258, 10007-10012
24. Johnston, T. C., Borgia, P. T., and Parker, J. (1984) *Mol. Gen. Genet.* 195, 459-465
25. Precup, J., and Parker, J. (1987) *J. Biol. Chem.* 262, 11351-11355
26. Barker, D. G., and Bruton, C. J. (1979) *J. Mol. Biol.* 133, 217-231
27. Mascarenhas, A. P., An, S., Rosen, A. E., Martinis, S. A., and Musier-Forsyth, K. (2009) in *Protein Engineering-Nucleic Acids and Molecular Biology Series* 22 (Kohrer, C., and RajBhandary, U. L., eds) 1st Ed., pp. 155-203, Springer-Verlag, Heidelberg, Germany
28. Splan, K. E., Musier-Forsyth, K., Boniecki, M. T., and Martinis, S. A. (2008) *Methods* 44, 119-128
29. Silvian, L. F., Wang, J., and Steitz, T. A. (1999) *Science* 285, 1074-1077
30. Tukalo, M., Yaremchuk, A., Fukunaga, R., Yokoyama, S., and Cusack, S. (2005) *Nat. Struct. Mol. Biol.* 12, 923-930
31. An, S., and Musier-Forsyth, K. (2005) *J. Biol. Chem.* 280, 34465-34472
32. Ruan, B., and Soll, D. (2005) *J. Biol. Chem.* 280, 25887-25891
33. Lincecum, T. L., Jr., Tukalo, M., Yaremchuk, A., Mursinna, R. S., Williams, A. M., Sproat, B. S., Van Den Eynde, W., Link, A., Van Calenbergh, S., Grotli, M., Martinis, S. A., and Cusack, S. (2003) *Mol. Cell.* 11, 951-963
34. Nomanbhoy, T. K., Hendrickson, T. L., and Schimmel, P. (1999) *Mol. Cell.* 4, 519-528
35. Gruic-Sovulj, I., Uter, N., Bullock, T., and Perona, J. J. (2005) *J. Biol. Chem.* 280, 23978-23986
36. Splan, K. E., Ignatov, M. E., and Musier-Forsyth, K. (2008) *J. Biol. Chem.* 283, 7128-7134
37. Hati, S., Ziervogel, B., Sternjohn, J., Wong, F. C., Nagan, M. C., Rosen, A. E., Siliciano, P. G., Chihade, J. W., and Musier Forsyth, K. (2006) *J. Biol. Chem.* 281, 27862-27872
38. Gruic-Sovulj, I., Rokov-Plavec, J., and Weygand-Durasevic, I. (2007) *FEBS Lett.* 581, 5110-5114
39. Berthet-Colominas, C., Seignovert, L, Hartlein, M., Grotli, M., Cusack, S., and Leberman, R. (1998) *EMBO J.* 17, 2947-2960
40. McClendon, C. L., Vaidehi, N., Kam, V. W., Zhang, D., and Goddard, W. A., 3rd (2006) *Protein Eng. Des. Sel.* 19, 195-203
41. Cusack, S. (1995) *Nat. Struct. Biol.* 2, 824-831
42. Sankaranarayanan, R., and Moras, D. (2001) *Acta Biochim. Pol.* 48, 323-335
43. Andrulis, I. L., Hatfield, G. W., and Arfin, S. M. (1979) *J. Biol. Chem.* 254, 10629-10633
44. Arfin, S. M., Simpson, D. R., Chiang, C. S., Andrulis, I. L., and Hatfield, G. W. (1977) *Proc. Natl. Acad. Sci. U.S.A.* 74, 2367-2369
45. Newberry, K. J., Hou, Y. M., and Perona, J. J. (2002) *EMBO J.* 21, 2778-2787
46. Ishitobi, M., Miyoshi, Y., Hasegawa, S., Egawa, C., Tamaki, Y., Monden, M., and Noguchi, S. (2003) *Cancer Lett.* 200, 1-7
47. Stanners, C. P., Wightman, T. M., and Harkins, J. L. (1978) *J. Cell. Physiol.* 95, 125-137
48. Lee, J. W., Beebe, K., Nangle, L. A., Jang, J., Longo-Guess, C. M., Cook, S. A., Davisson, M. T., Sundberg, J. P., Schimmel, P., and Ackerman, S. L. (2006) *Nature* 443, 50-55
49. Schimmel, P. (2008) *Protein Sci.* 17, 1643-1652
50. Park, S. G., Schimmel, P., and Kim, S. (2008) *Proc. Natl. Acad. Sci. U.S.A.* 105, 11043-11049
51. Poschl, E., Fox, J. W., Block, D., Mayer, U., and Timpl, R. (1994) *EMBO J.* 13, 3741-3747
52. Jnaoui, K., Minet, M., and Michiels, T. (2002) *J. Virol.* 76, 8138-8147
53. Stevens, C., Lin, Y., Sanchez, M., Amin, E., Copson, E., White, H., Durston, V., Eccles, D. M., and Hupp, T. (2007) *J. Biol. Chem.* 282, 13791-13803
54. Kaye, E. M., Shalish, C., Livermore, J., Taylor, H. A., Stevenson, R. E., and Breakefield, X. O. (1997) *J. Child Neurol.* 12, 242-247

55. George, E., Huisman, T. H., Yang, K. G., Kutlari, F., Wilson, J. B., Kutlar, A., Storming, T. A., Gonzales-Redondo, J. M., Faridah, K., and Khalid, A. K. (1989) *Med. J. Malaysia* 44, 259-262

56. Walz, R., Castro, R. M., Landemberger, M. C., Velasco, T. R., Terra-Bustamante, V. C., Bastos, A. C., Bianchin, M., Wichert-Ana, L., Arau'jo, D., Alexandre, V., Jr., Santos, A. C., Machado, H. R., Carlotti, C. G., Jr., Brentani, R. R., Martins, V. R., and Sakamoto, A. C. (2004) *Neurology* 63, 557-560

57. Klannemark, M., Suurinkeroinen, L., Orho-Melander, M., Groop, L., and Taskinen, M. R. (2000) *Diabet. Med.* 17, 599-605

Example 2

Substitutions of amino acids in the primary sequence of a protein are known to occur in nature. Typically mutations occur at the DNA level and then get translated into protein (Santos and Tuite 1993). Protein variants are a special concern during biopharmaceutical protein production in terms of impact on protein activity and immunogenicity (Rosenberger and Holliday, *Trends in Biotechnology* 11:498-499 (1993)). During recombinant protein production in mammalian cell culture, variant sequences for point mutations have been known to be introduced in production cell lines. A variant form of antibody gene sequence was found to be developed during the transfection of antibody light and heavy chain genes into CHO cells (Harris et al. *Bio-Technology* 11:1293-1297 (1993)). A polyclonal population of cells with the variant and the normal form of the gene, led to the fraction of the variant form to vary with cell age. In a more recent study, CHO subclones with 20-24 copies of the gene for the fusion protein integrated into the genome exhibited a Phe→Leu substitution in the product (Dorai et al. *Bioprocess International* 5:66-72 (2007)). About 12% of the mRNAs were estimated to have the mutation whereas the rest were per expectation, indicating that only a fraction of the integrated copies were mutated.

Substitution has been found to occur during protein synthesis also. This has been well established in ribosomal and non-ribosomal synthesis of peptides and proteins in prokaryotic systems (Petersen et al. *J Ind Microbiol Biotechnol.* 26:216-21 (2001); Santos and Tuite 1993). Mistranslations can be the result of aberrant initiation, a frame shift, a missense error, tRNA hopping, or a termination bypass. In *E. coli* missense errors occur at frequencies of $5 \times 10^{-3}$ to $1 \times 10^{-5}$ (Santos and Tuite 1993). In extreme cases of imbalance, increased protein heterogeneity due to misincorporation has been observed. Mistranslation has been reported for a number of cases in *E. coli* where rare codons are present in sequence of the heterologous protein being overexpressed (McNulty D E et al., *Protein Expression and Purification* 27:365-374 (2003); Calderone T L, et al. *Journal of Molecular Biology* 262:407-412 (1996); Schneider E L, et al., *Biochemistry* 44:987-995 (2005); Bogosian G, *Journal of Biological Chemistry* 264:531-539 (1989); Seetharam R et al., *Biochemical and Biophysical Research Communications* 155:518-523 (1988); Lu H S, et al., *Protein Expression and Purification* 4:465-472 (1993); Lu H S, et al., *Biochemical and Biophysical Research Communications* 156:807-813 (1988)). In some of these, concomitant expression of the rare codon tRNA gene eliminated the misincorporation. In one reported case, a limitation of methionine lead to substitution with norleucine (Bogosian, 1989; Kane J F, et al., *Curr Opin Biotechnol.* 6:494-500 (1995); Tsai L B, et al., *Biochemical and Biophysical Research Communications* 156:733-739 (1988)). Extent of mistranslation has also been found correlated to rates of protein synthesis, substitution being significantly higher at high expression rates (Schneider et al. 2005). Amino acid misincorporation due to the presence of rare codons in abundant mRNA, or due to stress induced by amino acid starvation has been viewed as a direct consequence of aminoacyl-tRNA limitation, allowing the translational machinery to insert an incorrect amino acid at the paused ribosome (Santos and Tuite 1993). Thus, using proper codons favorable to the host organism used, amino acid incorporation in the medium, simultaneous expression of the rare tRNA, or reducing expression rates are some of the strategies that have been successfully used to reduce extent of misincorporation in microbial systems.

A substitution was found to occur in a CHO cell process in our laboratories (Wen, D., et al., *J. Biol. Chem.* jbc.M109.059360, First Published on Sep. 25, 2009). Monoclonal antibody A produced by a CHO cell line was found to have one or more of 21 out of 25 residues of Asparagine replaced by Serine. The phenomenon was found not to be cell line or product specific. It was found that supplementation of media with asparagine eliminated occurrence of substitution at shake flask scale. This indicates that the phenomenon may be caused by starvation of a particular amino acid as observed previously (Parker et al. *Proc. Nat'l Acad. Sci. USA* 75:1091-1095 (1978)).

Current recombinant cell culture processes are achieving cell density 2-8 fold higher than observed 10 years ago. This has put additional stress on cells to maintain consistent production of recombinant proteins. We decided to further investigate and define the phenomenon in order to develop a robust solution to the problem of product quality variability. There are two potential mechanistic root causes at the cell level to explain the occurrence of substitution (a) depletion of asparagines could be leading to reduced tRNAasn causing tRNAser to substitute for due to mistranslation and (b) excess Serine versus Asparagine could be leading to serine substituting for Asparagine on tRNAasn. Cell culture medium/feed composition and feed control strategy is hypothesized as a cause of the substitution, given that it has been observed in two cell lines expressing different antibodies, both grown in same process format.

Materials and Methods

Cell line and culture medium details: Cell lines expressing Antibody A were generated by transfecting CHO DG44 host with the light chain and heavy chain genes and selecting for expression. The host cell line had been previously adapted for growth in serum free medium (Prentice et al. 2007). Two cell lines (13-21 and 15-29) expressing antibody A were characterized for the purposes of this study. 13-21 had a faster specific asparagine uptake rate relative to the 15-29 cell line. A proprietary basal medium containing asparagine, serine and glutamine and feed medium containing asparagine and serine was used for the protein expression. Both media contained protein hydrolysates. For serine impact specific studies, medium with identical composition to basal and feed medium, but with no serine and asparagine, was used. Asparagine and Serine were dosed in separately as needed.

Bioreactor and shake flask culture: Culture in 5-L bioreactors with 3 L working volumes were grown at 35° C., pH 7.1±0.2 and dissolved oxygen concentration of 30% air saturation for 14 days. Fixed feed amounts were added starting Day 3. Shake-flask studies were carried out in 500 mL flasks with 100 mL working volume. Agitation in orbital shakers at 125 rpm was previously established to be sufficient to maintain oxygen levels to support cell density up to $12-15 \times 10^{6}$ viable cells/mL.

Offline Analysis: Cell growth and viability were measured by means of Trypan blue exclusion using an automatic Cedex instrument (Innovatis AG, Germany). The antibody concentration was measured using an HPLC with a UV detector, and a protein G affinity column (Applied Biosystems, CA).

Amino acid analysis: Amino acid quantification was carried out by HPLC based separation and analysis of precolumn derivatized samples using a modified OPA/FMOC method (Henderson et al. 2000). The derivatized amino acids were separated by reverse phased HPLC.

Peptide substitution analysis: A rapid and sensitive LC-MS based assay focusing on three peptides out of ~50 possible peptides was used as a screening tool to identify instances of substitution and to get a quantitative estimate of the extent of substitution. The antibody protein was purified at small scale using protein A columns. Reduction and denaturation of antibody A were carried out followed by digestion with Lysyl Endopeptidase for approximately 18-20 hours at 25° C. A HPLC gradient based separation was carried out subsequently and the individual peptides were analyzed by Q-TOF MS system. Three specific peptides were looked at in detail by mass spectrometry. A 27 Da shift was observed for asparagine to serine substitution.

Results

Figure 7:
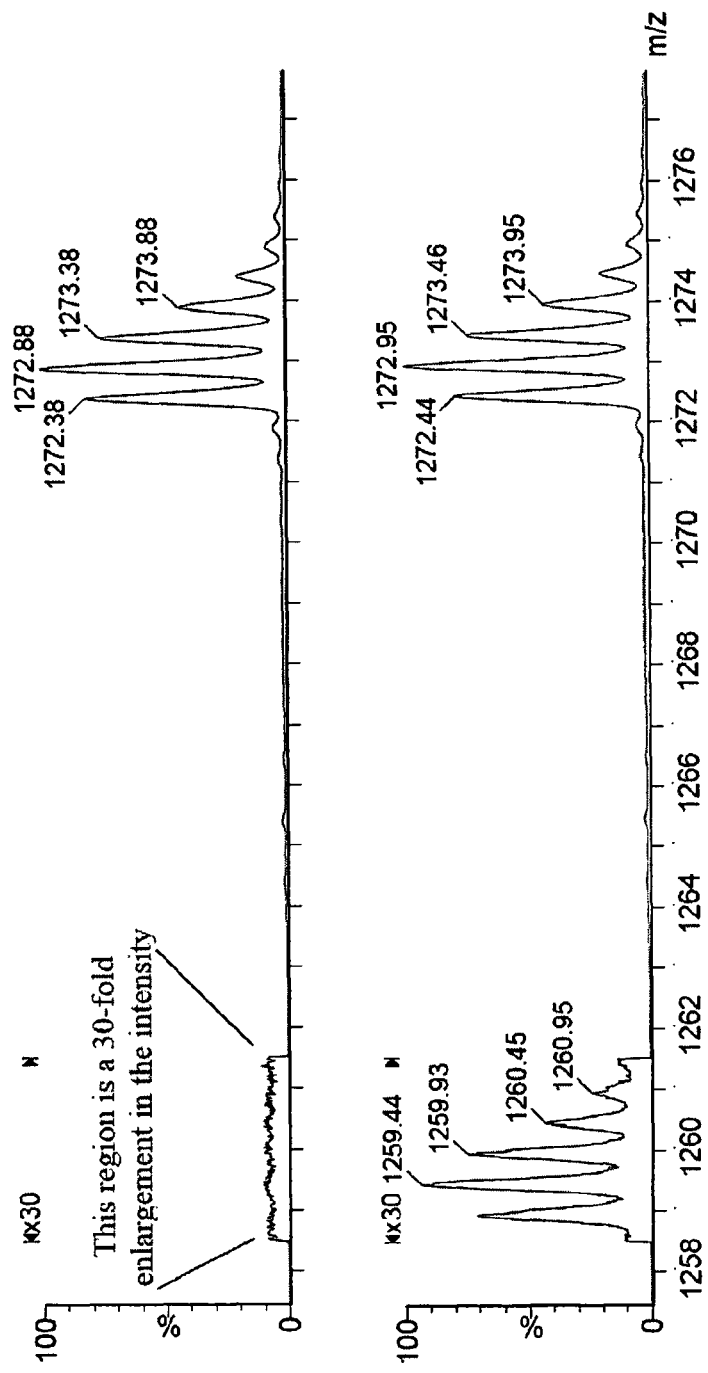
FIG. 7. Peptide map analysis followed by mass spectroscopy revealed the presence of substitution corresponding to asparagine to serine misincorporation. (a) sample with no substitution (b) sample with substitution. Molecular weight shift in figure corresponds to half of 27 Da.

Peptide Map analysis—Peptide fragments separated by HPLC were analyzed by mass spectroscopy as shown in FIG. 7. For the control sample without substitution, there are multiple peaks for the fragment corresponding to isotope ratios of carbon. Region corresponding to −27 Da showed no presence of additional peaks. For another sample, additional peaks were observed at the −27 Da position upon 30-fold enlargement of intensity. Based on additional analysis, this was attributed to substitution of Serine for Asparagine.

Figure 8:
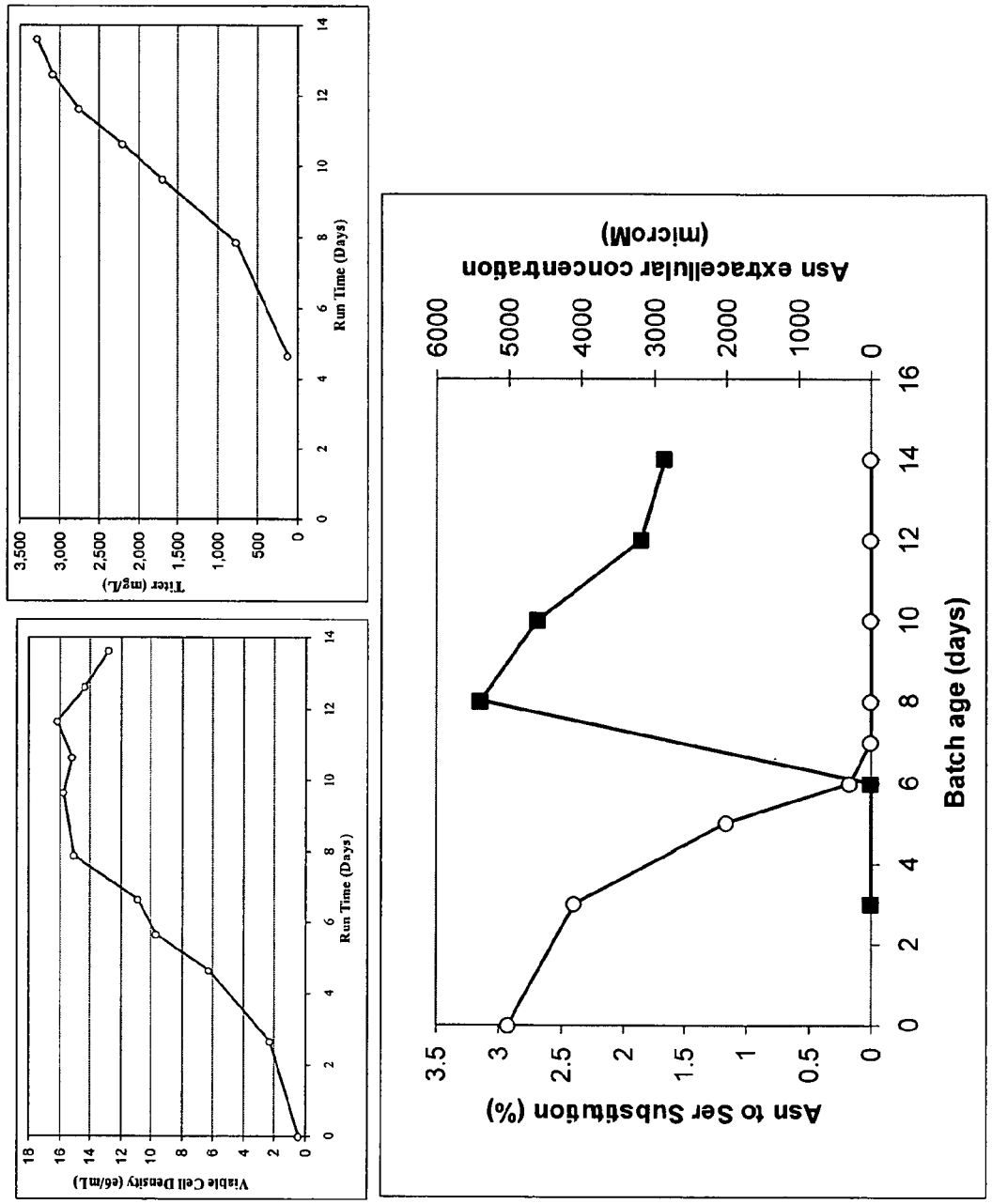
FIG. 8. Time course analysis of the phenomenon of substitution. (a) Viable cell density and mAB Titer profile and (b) Extracellular concentration of Asparagine (open circles) and % substitution of asparagine to serine (closed squares). Maximum substitution was observed after depletion of Asparagine in the medium.

Time course analysis—A time course analysis was carried out using the 13-21 cell line. Cells were grown in fed-batch mode with basal and feed media. The viable cell density of the culture increased to 16E6 vc/mL by Day 8 ending growth phase and entering the stationary phase. The titer profile continued to increase over the course of the 14 day culture. A time course of samples was collected and processed via mass spec analysis. The extent of substitution was quantified in a relative manner. The extent of substitution was zero through day 7 and had a sharp increase on day 8 corresponding to the time when the concentration of asparagine in the medium reduced to zero. The time course of substitution with serine correlated with depletion of asparagine below detection level (FIG. 8). Interestingly in following the time course further, the percentage substitution reduced to lower levels following the peak observed on Day 8.

Figure 9:
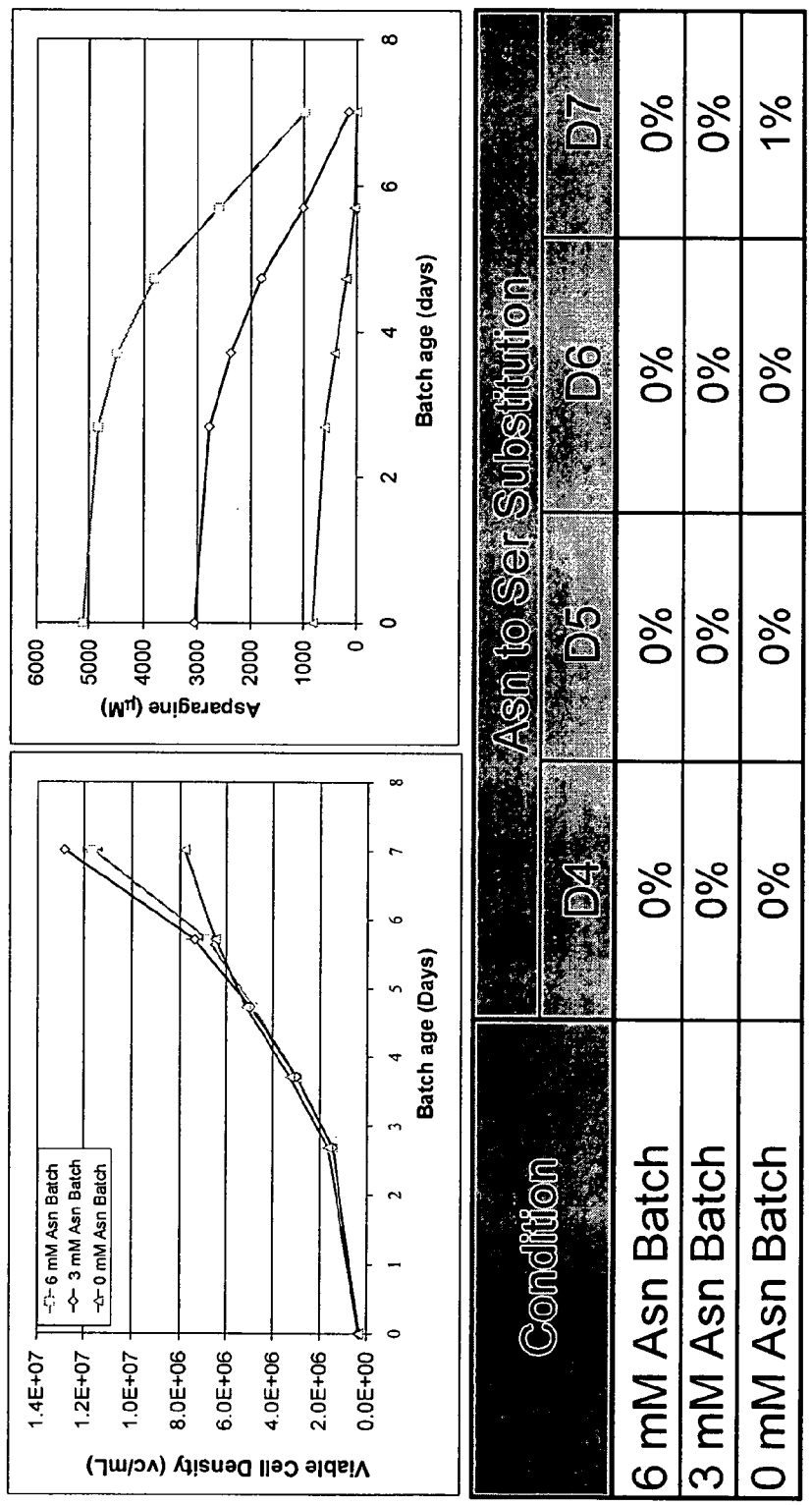
FIG. 9. Shake flask experiment with varying starting concentration of Asparagine. Substitution was observed only in the culture with no Asparagine supplementation, upon exhaustion of Asparagine in the medium. Cell growth flattening is correlated to depletion of Asparagine.

Correlation to disappearance of Asparagine in medium: Following the observation that asparagine depletion corresponded to the onset of substitution with cell line 13-21, a different cell line 15-29 which had a lower specific uptake rate of asparagine was used for further work. This cell line was used to characterize if the presence of high serine or absence of asparagine is the root cause of the observed substitution. To study effect of low asparagine, samples from shake flask culture with variable initial concentration of asparagine ranging from 0-6 mM were evaluated in 7 day batch culture. Growth, amino acid concentration in the medium, and asparagine to serine substitution were monitored. Only the flask with a low starting concentration of Asparagine showed substitutions on the final time point monitored. This timepoint correlated to depletion of Asparagine in medium. (FIG. 9).

Impact of serine concentration on substitution: Impact of serine was tested under high and low levels of starting asparagine concentrations. Under high asparagine starting concentration of 6 mM, no substitution was observed even though Serine levels were increased to as high as 13 mM. Low concentration of asparagine was a necessary condition for all observed substitutions.

Figure 10:
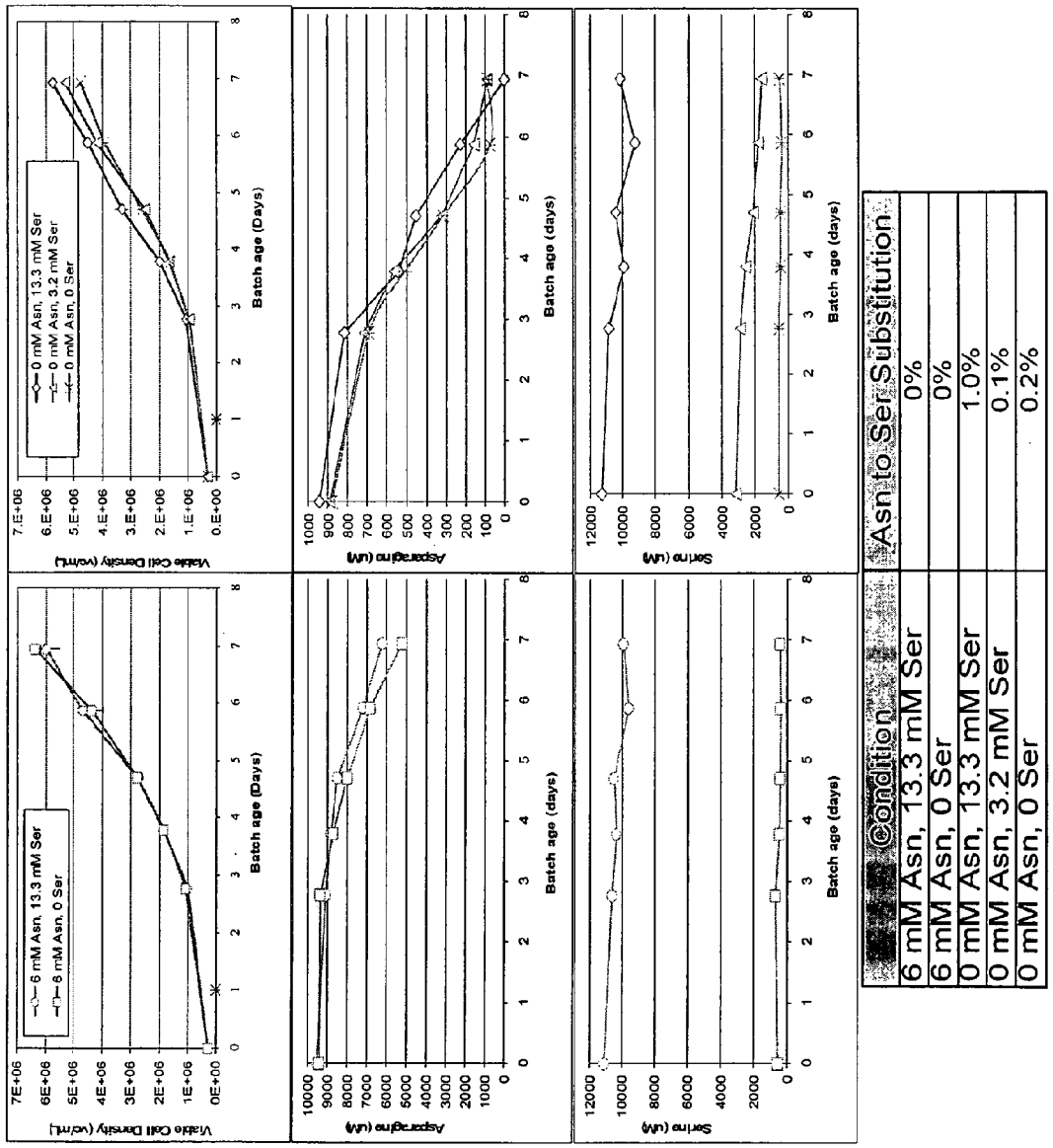
FIG. 10. Shake flask experiment with serine present in basal and feed media was reduced to zero under high asparagine or low asparagine conditions. Substitution was not observed when Asparagine levels were high even though Serine levels were high. Conversely, substitution was observed in each case where asparagine was depleted from the media, both under low and high serine concentrations in the media. High serine concentrations were correlated to a higher extent of substitution.

In conditions with 0 mM asparagine supplementation, some asparagine was present as a carryover from the inoculum stage. Under these conditions, the asparagine concentration was reduced to approximately 0.1 mM or less by Day 6. With supplemented serine levels varied from 0 mM to 13 mM, substitution was observed in all cases. A high level of serine (13 mM) under low concentrations of Asparagine seemed to exacerbate the extent of substitution and lower concentrations of serine were correlated to lower levels of substitution (FIG. 10).

Figure 11:
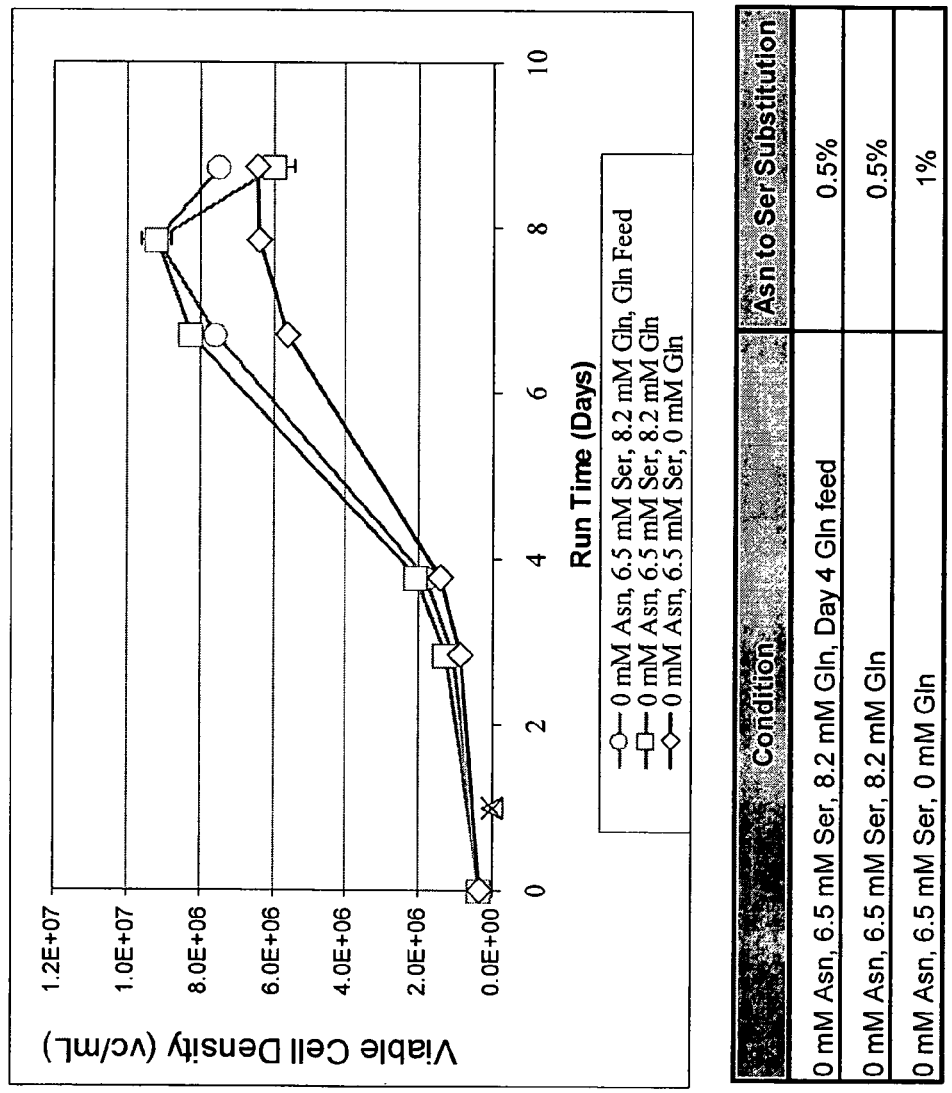
FIG. 11. Shake flask experiment with glutamine supplementation reduced extent of substitution.

Impact of glutamine supplementation on substitution: Since asparagine is a nonessential amino acid which can be supplied by biosynthesis within CHO cells, supplementation with glutamine was explored as an alternative means to eliminate substitution. Shake flasks with medium supplemented with 8.2 mM Glutamine in the batched medium and that with an additional Day 4 additional feed of glutamine had reduced substitution levels relative to the negative control (FIG. 11).

Figure 12:
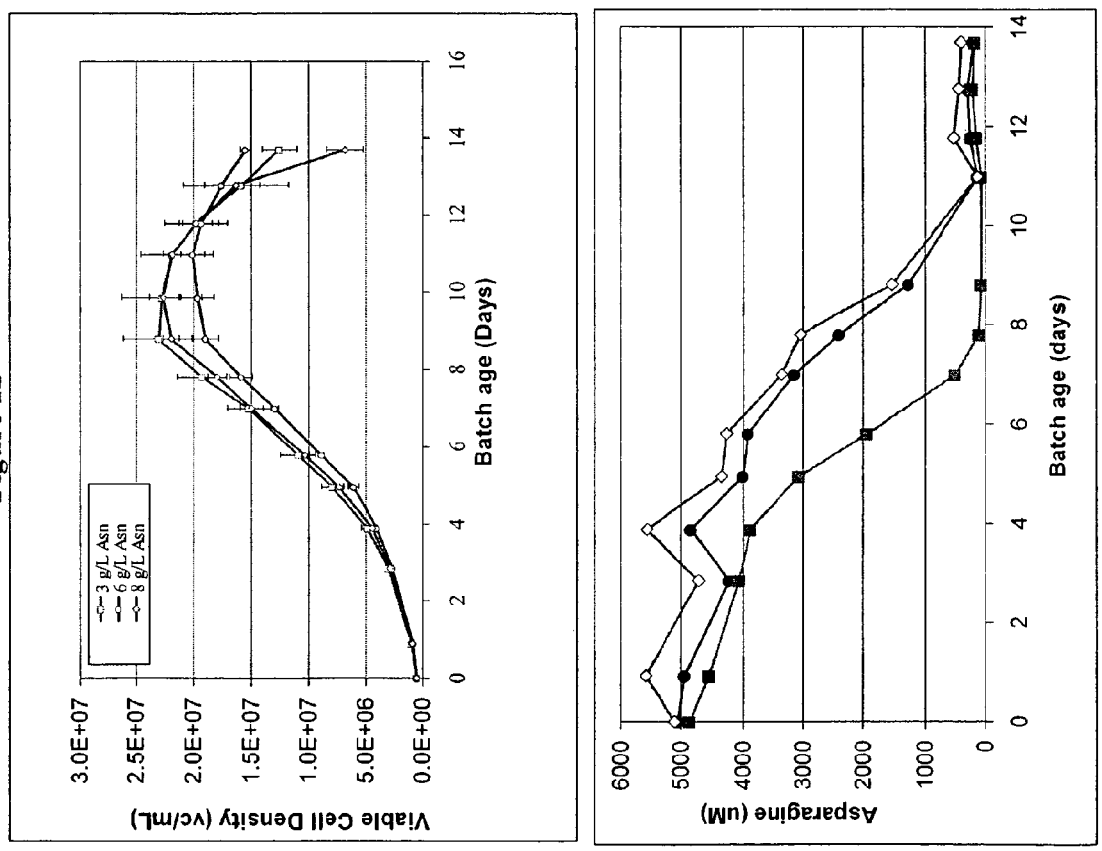
FIG. 12. Asparagine profiles of three cultures fed different amounts of asparagine. The initial asparagine concentrations are the same with feeds supplemented with 3 g/L Asparagine, 6 g/L Asparagine and 8 g/L Asparagine.

Optimization of Asparagine supplementation: In an effort to prevent asparagine depletion in the medium while simultaneously controlling the extent of ammonium ions produced due to its degradation, asparagine was supplemented in the feed. Three different asparagine supplementation concentrations in the feed were explored in a bioreactor experiment ranging from 3 g/L to 8 g/L. The highest concentration had a risk of higher ammonia levels impacting product quality. The lowest concentration had risk of substitutions with borderline substitution detected in the product (data not shown). Thus 6 g/L asparagine supplementation in the feed medium was picked as the optimal concentration (FIG. 12). Interestingly, even though the asparagine concentration in the medium drops to very low levels on Day 8-10 for the 6 g/L and 8 g/L conditions, no substitution was observed in either of these conditions. This observation points to both the amount of asparagine added and time of depletion as factors impacting the extent of substitution. Depletion of asparagine at a later stage in culture does not appear to lead to substitution.

Figure 13:
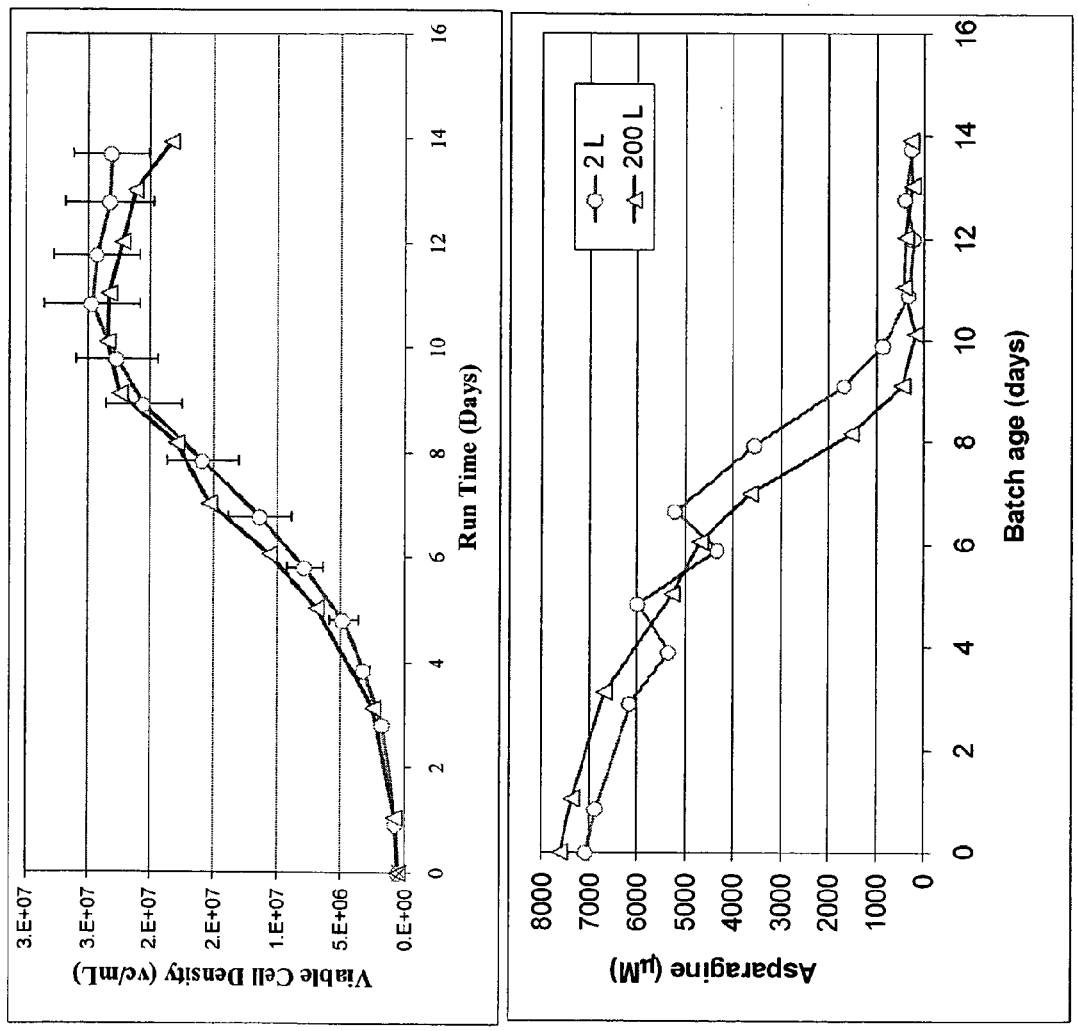
FIG. 13. Impact of scale-up on substitution was tested at 2 L and 200 L scales. Asparagine profiles were per prediction and no substitution was observed across multiple batches.

Asparagine Supplementation as a Robust Solution:

Following bench scale development, the process with 6 g/L Asparagine supplemented in the feed was scaled-up to 200 L (FIG. 13) and subsequently to 2000 L. No substitution was observed in multiple cell culture runs at either of these scales. Depletion of asparagine to low levels was observed on Days 8-10 in culture. Nonetheless, based on the product analysis the sensitivity to substitution was not impacted by the scale of operation.

Effect of Temperature and Supplementation on Substitutions:

A bioreactor evaluation of one cell line was performed with a very low level of Asn added (0.12 g/L) at 28° C. and had no measurable misincorporation. Bioreactor evaluations of a second cell line were performed with a higher level of Asn added (0.42 g/L) at either 36.5° C. or 35° C. The run at 36.5° C. had 4% misincorporation while the 3 runs at 35° C. had the same or lower levels of misincorporation (2%, 3%, 4%). Finally, bioreactor evaluations of a third cell line were performed with the same level of total Asn added (0.42 g/L) at either 36.5° C. or 35° C. The run at 36.5° C. had 4% misincorporation while the 2 runs at 35° C. had the same or lower levels of misincorporation (2%, 4%). Cultures at lower temperatures tended to produce lower levels of misincorporation. Thus, it appears that misincorporation can be reduced by up to half by reducing the temperature from 36.5° C. to 35° C.

Discussion

Numerous examples have been documented for misincorporation in recombinant microbial expression systems correlated to either a depletion of the amino acid or the lack of tRNA needed. The observation characterized in this study is the first reported instance of recombinant expression in animal cells where a depletion of amino acid triggered misincorporation. DNA sequence was verified to be intact for all instances where misincorporation was observed and no bias related to codon was observed in the instances wherein misincorporation was observed. Similarly expression in different cell lines as well as with different antibody constructs demonstrated that it was not related to a specific mutation in the host or the vector construct (data not shown).

Asparagine in the medium is used for protein synthesis for growth and recombinant protein expression. Asparagine from the medium is being transported into the cell and intracellular concentration is also augmented by asparagine from internal turnover or synthesis. This available asparagine flux is channeled towards the synthesis of host cell proteins and recombinant protein expression. The demand for asparagine is likely maximal under growth phase, where demand for amino acids in general including that for asparagine for host cell protein synthesis should be maximal. Substitution was observed when asparagine in the external medium was reduced to very low values during growth phase. Under such a condition, it is likely that the lower intake of asparagine due to low external concentration, coupled with increased demand leads to imbalance and limitation. Alternatively it is possible that excess Serine in the medium leads to substitution. However no substitution was observed in instances where asparagine extracellular concentration reduced to zero in later stages of the culture and a lot of serine accumulated in the medium (data not shown). It is likely that towards the latter half of the fed-batch, the internal synthesis of asparagine was adequate to supply needs for recombinant protein as needs for host cell protein were reduced. Thus, even when external supply of asparagine is not substantial, internal synthesis is able to compensate and no substitution occurs. A supplementation of internal synthesis is also the likely explanation for the reduction in substitution when Glutamine is supplemented in the medium.

A similar reason is likely to explain the decreasing extent of substitution upon extended fed-batch culture as observed with cell line 13-21 (FIG. 2). Antibody is continually synthesized in the fed-batch culture. If fresh antibody that is synthesized occurs in a milieu where the cell does not experience asparagine limitation, it is likely not having misincorporation. Thus as additional antibody is synthesized; the extent of substitution in the overall protein secreted could keep decreasing.

It is clear from the current experiments that asparagine levels in the medium need to be reduced to low levels for substitution. Nonetheless, it is not clear which is the basic mechanism underlying the substitution. The observation that reducing serine concentration is correlated with lower substitution levels (FIG. 4) does not favor either of the two possible scenarios as the preferred underlying mechanism. Serine codons share first and third base pairs to that for Asparagine. While not conforming exactly with the wobble hypothesis at third pair, nonetheless a number of examples exist in microbial systems where substitution occurs upon a 2 out of 3 codon match (Laughrea et al. *Eur. J. Biochem.* 169:59-64 (1987)). The extent of aminoacylation of tRNAAsn has been found to decrease under conditions where asparagine is limiting (Andrulis et al. *J. Biol. Chem.* 254:629-633 (1979)). Under these conditions, serine substitution could occur for asparagine due to utilization of tRNAser instead of tRNAasn. Nonetheless, with this hypothesis, an explanation is lacking as to why Lysine, which shares first and second codons with Asparagine and only differs in the third codon, is not being substituted instead.

In the alternate scenario, tRNAasn could be misloaded with Serine under lower intracellular concentrations of Asparagine. As enunciated by Wen et. al., Asparagine and Serine are neutral, polar amino acids and among other characteristics their apparent partial specific volumes are very similar (Wen et al. 2009). It is calculated that serine would compete with Asparagine for formation of an activated intermediate with asparaginyl-tRNA-synthetase. If true, this would explain why a specific Asparagine to Serine substitution is being favored.

Overall, it appears that CHO cells are subject to similar issues of substitution as observed in microbial cells and thus monitoring of amino acid concentrations in the medium and use of mass spectrometer based methods to characterize product is prudent to assure absence of heterogeneity.

What is claimed is:

1. A method for preventing misincorporation of serine in place of asparagine during translation of a polypeptide of interest in a mammalian cell, comprising:
   (a) providing a culture comprising the cell in growth media, wherein the culture has a volume of at least 500 liters;
   (b) supplementing the culture with a feed medium comprising asparagine, or a metabolic precursor thereof, in an amount sufficient to reduce serine misincorporation; and
   (c) maintaining the supplemented culture under conditions appropriate for expression of the polypeptide of interest, wherein the polypeptide of interest expressed by the cell comprises less than about 3% serine misincorporated in place of asparagine.

2. The method of claim 1, wherein the supplementing is performed during the growth phase.

3. The method of claim 1, wherein the supplementing is performed prior to depletion of asparagine from the culture.

4. The method of claim 1, wherein the feed medium comprises more than about 3 g/L of asparagine.

5. The method of claim 1, wherein the mammalian cell is selected from the group consisting of: chinese hamster ovary (CHO), monkey kidney CV1, monkey kidney COS, human lens epithelium, human embryonic kidney, baby hamster kidney, african green monkey kidney, human cervical carcinoma, canine kidney, buffalo rat liver, human lung, human liver, mouse mammary tumor, hybridoma and myeloma cell lines.

6. The method of claim 1, wherein the culture is supplemented with the feed medium at multiple intervals.

7. The method of claim 1, wherein the polypeptide of interest is selected from the group consisting of: antibody, antibody fragment, enzyme, receptor, hormone, regulatory factor, growth factor, antigen, and binding agent.

8. The method of claim 7, wherein the polypeptide is an antibody that specifically binds TWEAK.

9. The method of claim 1, wherein the polypeptide of interest expressed by the cell comprises less than about 1%, or less than about 0.1% of serine misincorporated in place of asparagine.

10. The method of claim 1, wherein the serine concentration of the feed medium is the same or lower than the serine concentration of the growth media.

11. The method of claim 1, wherein the feed medium comprises more than about 6 g/L of asparagine.

12. The method of claim 1, wherein the feed medium comprises glutamine in an amount sufficient to reduce serine misincorporation.

13. The method of claim 12, wherein the supplemented culture comprises between about 1 mM to about 10 mM glutamine.

14. The method of claim 1, wherein the supplemented culture comprises between about 1 nM to about 10 mM asparagine.

15. The method of claim 1, wherein the supplementing is performed during the growth and production phases.

16. The method of claim 1, wherein the supplementing is done at a frequency and level such that the amount of asparagine in the growth medium does not fall below detectable levels during growth phase.

17. The method of claim 1, wherein the supplementing is done at a frequency and level such that the amount of asparagine does not fall below 0.1 mM during growth phase.

* * * * *